(12) United States Patent
Schoon et al.

(10) Patent No.: US 9,918,881 B2
(45) Date of Patent: Mar. 20, 2018

(54) METHOD OF FOLDING PANT-LIKE DISPOSABLE ABSORBENT GARMENTS IN A TROUGH

(75) Inventors: Bradley Schoon, Oshkosh, WI (US); Brian R. Vogt, Winneconne, WI (US); Stephen A. Kolasinski, New London, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1705 days.

(21) Appl. No.: 13/302,429

(22) Filed: Nov. 22, 2011

(65) Prior Publication Data
US 2013/0130879 A1 May 23, 2013

(51) Int. Cl.
*B31F 1/00* (2006.01)
*A61F 13/15* (2006.01)
*A61F 13/496* (2006.01)

(52) U.S. Cl.
CPC ...... *A61F 13/15747* (2013.01); *A61F 13/496* (2013.01)

(58) Field of Classification Search
CPC ......... B65B 63/045; B65B 25/20; B65B 5/00; B65D 85/18; B65D 85/16; B65D 85/08; A61F 13/551; A61F 13/15747; A61F 13/55115
See application file for complete search history.

(56) References Cited

U.S. PATENT DOCUMENTS

| 3,572,689 A | 3/1971 | Murphy |
| 3,635,462 A * | 1/1972 | Joa ............................... 493/394 |
| 4,326,528 A | 4/1982 | Ryan |
| 4,614,512 A | 9/1986 | Capdeboscq |
| 4,701,156 A | 10/1987 | Larsonneur |

(Continued)

FOREIGN PATENT DOCUMENTS

| CN | 1770989 A | 5/2006 |
| EP | 0 119 827 B1 | 7/1988 |

(Continued)

OTHER PUBLICATIONS

Co-pending U.S. Appl. No. 13/302,508, filed Nov. 22, 2011, by Sieck et al. for "Method of Folding Pant-Like Disposable Absorbent Garments in a Chute."

*Primary Examiner* — Michelle Lopez
*Assistant Examiner* — Chinyere Rushing-Tucker
(74) *Attorney, Agent, or Firm* — Kimberly-Clark Worldwide, Inc.

(57) ABSTRACT

A method of folding a pant-like disposable absorbent garment includes providing a garment defining first and second waist side regions, a waist center region positioned therebetween, and a crotch region longitudinally below the waist center region. In particular embodiments, the method further includes folding the garment along a transversely extending fold line so as to bring the crotch region into superposed relation with the waist center region; providing a trough having a floor and first and second side walls; placing the waist center region in the trough; and, while the garment is in the trough, folding the garment along longitudinally extending first and second fold lines so as to position the first and second waist side regions, respectively, over the waist center region. The first and second fold lines are adjacent the first and second side walls, respectively.

15 Claims, 23 Drawing Sheets

(56) References Cited

U.S. PATENT DOCUMENTS

| | | | |
|---|---|---|---|
| 5,046,272 A | 9/1991 | Vogt et al. | |
| 5,300,007 A | 4/1994 | Kober | |
| 5,601,547 A | 2/1997 | Kato et al. | |
| 5,776,121 A | 7/1998 | Roe et al. | |
| 5,868,727 A * | 2/1999 | Barr et al. | 604/387 |
| 6,015,934 A | 1/2000 | Lee et al. | |
| 6,305,146 B1 | 10/2001 | Gerber | |
| 6,514,187 B2 | 2/2003 | Coenen et al. | |
| 6,601,705 B2 | 8/2003 | Molina | |
| 6,635,462 B1 | 10/2003 | Ensor et al. | |
| 6,669,618 B2 | 12/2003 | Reising et al. | |
| 6,699,166 B2 | 3/2004 | Walter et al. | |
| 6,723,035 B2 * | 4/2004 | Franklin et al. | 493/450 |
| 6,846,374 B2 | 1/2005 | Popp et al. | |
| 6,923,926 B2 | 8/2005 | Walter et al. | |
| 7,021,466 B2 | 4/2006 | Kuske | |
| 7,150,137 B2 | 12/2006 | Tippey | |
| 7,399,266 B2 | 7/2008 | Aiolfi | |
| 7,500,941 B2 * | 3/2009 | Coe et al. | 493/438 |
| 7,617,656 B2 | 11/2009 | Wiedmann | |
| 8,440,039 B2 | 5/2013 | Nakakado | |
| 8,496,778 B2 | 7/2013 | Vasic | |
| 8,663,411 B2 | 3/2014 | McCabe | |
| 8,672,824 B2 | 3/2014 | Sablone et al. | |
| 2003/0062113 A1 | 4/2003 | Van Eperen et al. | |
| 2003/0226862 A1 | 12/2003 | Vogt et al. | |
| 2004/0048727 A1 | 3/2004 | Roozrokh | |
| 2004/0054342 A1 | 3/2004 | Newbill et al. | |
| 2004/0185996 A1 | 9/2004 | Franklin et al. | |
| 2007/0107918 A1 | 5/2007 | Coe et al. | |
| 2007/0129230 A1 * | 6/2007 | Sosalla | 493/441 |
| 2007/0142194 A1 * | 6/2007 | Coenen et al. | 493/405 |
| 2007/0144937 A1 | 6/2007 | Gilroy | |
| 2007/0267322 A1 | 11/2007 | Kishida | |
| 2008/0134641 A1 | 6/2008 | Corlett | |
| 2008/0276570 A1 | 11/2008 | Kuroda et al. | |
| 2009/0299321 A1 * | 12/2009 | Uda | 604/385.201 |
| 2010/0072108 A1 | 3/2010 | Underhill | |
| 2010/0179042 A1 | 7/2010 | Yamamoto | |
| 2011/0209269 A1 | 9/2011 | Kinoshita et al. | |
| 2011/0251038 A1 | 10/2011 | Lavon et al. | |
| 2012/0028777 A1 | 2/2012 | Knecht | |
| 2012/0043244 A1 * | 2/2012 | Hagner et al. | 206/459.5 |
| 2012/0043245 A1 * | 2/2012 | Hagner et al. | 206/459.5 |
| 2012/0077661 A1 | 3/2012 | Oonishi et al. | |
| 2012/0083399 A1 | 4/2012 | Putzer et al. | |
| 2012/0095429 A1 | 4/2012 | Kobayashi et al. | |
| 2012/0152447 A1 | 6/2012 | Schneider | |
| 2012/0172828 A1 | 7/2012 | Koenig et al. | |
| 2012/0208688 A1 | 8/2012 | Sakaguchi et al. | |
| 2012/0225764 A1 | 9/2012 | Ogasawara | |
| 2012/0324633 A1 | 12/2012 | Bäck et al. | |
| 2013/0296152 A1 | 11/2013 | Murakami et al. | |
| 2014/0378287 A1 | 12/2014 | Schneider et al. | |

FOREIGN PATENT DOCUMENTS

| | | |
|---|---|---|
| EP | 0 452 951 B1 | 11/1995 |
| EP | 1 933 796 B1 | 7/2010 |
| EP | 1 954 230 B1 | 1/2011 |
| JP | 58-013704 A | 1/1983 |
| JP | 01-009177 A | 1/1989 |
| JP | 04-266360 A | 9/1992 |
| JP | 09-099903 A | 4/1997 |
| JP | 09-131364 A | 5/1997 |
| JP | 10-095481 A | 4/1998 |
| JP | 11-113956 A | 4/1999 |
| JP | 2994345 B1 | 12/1999 |
| JP | 2000-024029 A | 1/2000 |
| JP | 2000-024030 A | 1/2000 |
| JP | 2001-019070 A | 1/2001 |
| JP | 2003-093436 A | 4/2003 |
| JP | 2003-250826 A | 9/2003 |
| JP | 2004-248785 A | 9/2004 |
| JP | 2006-247429 A | 9/2006 |
| WO | WO 2002/007665 A1 | 1/2002 |
| WO | WO 2004/108043 A1 | 12/2004 |
| WO | WO 2008/155702 A1 | 12/2008 |
| WO | WO 2009/083788 A1 | 7/2009 |
| WO | WO 2010/089964 A1 | 8/2010 |
| WO | WO 2010/101277 A1 | 9/2010 |

* cited by examiner

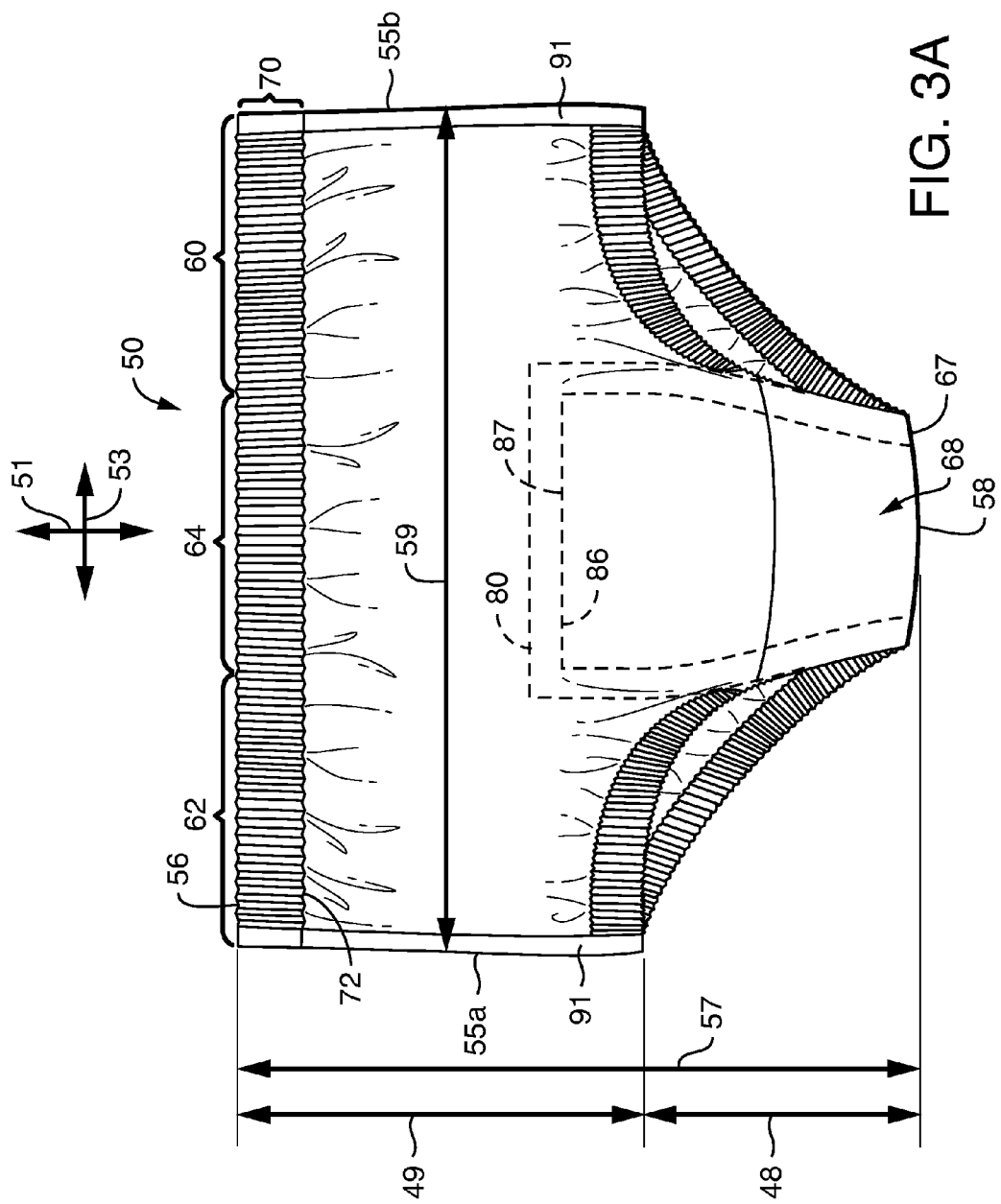

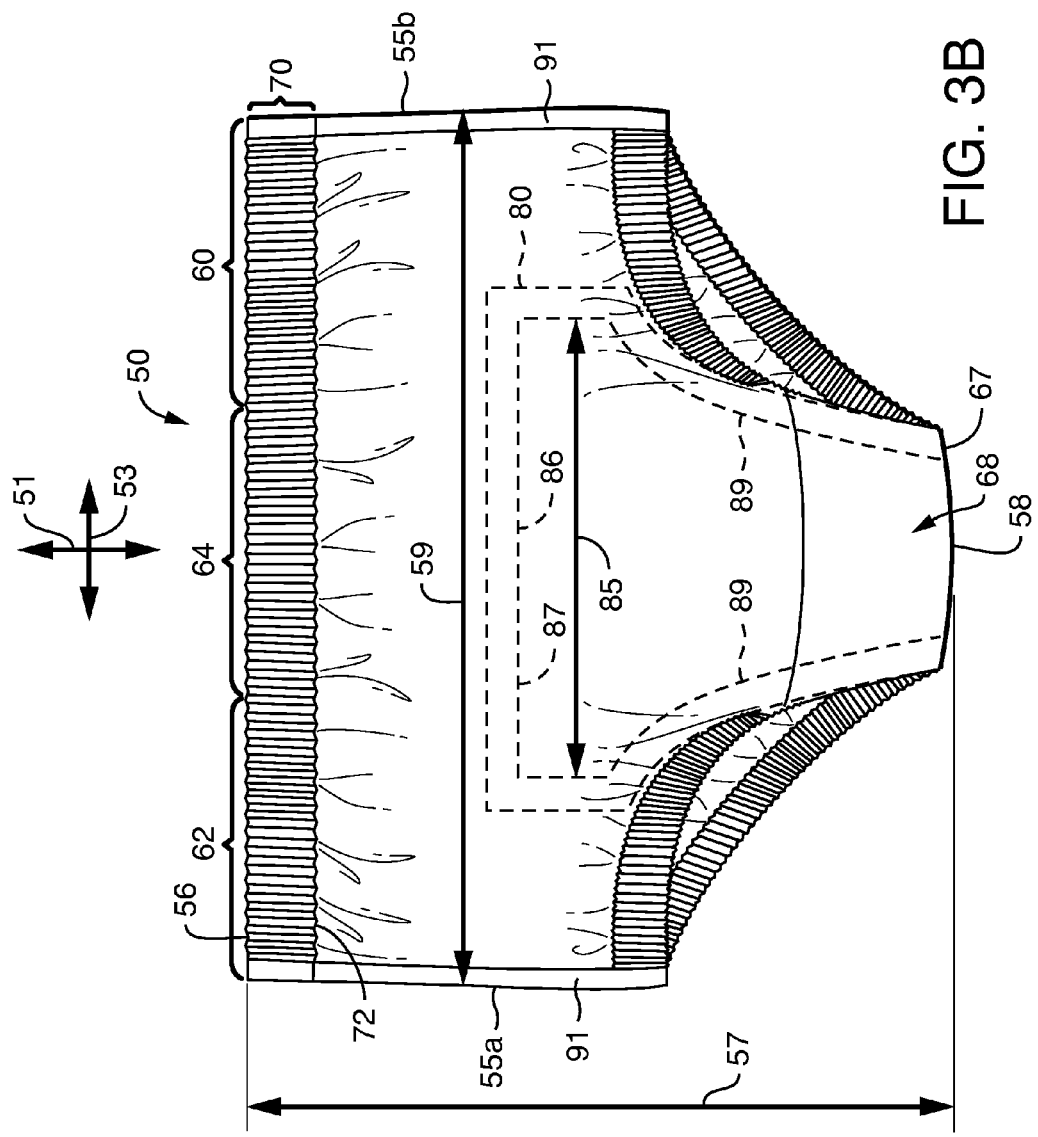

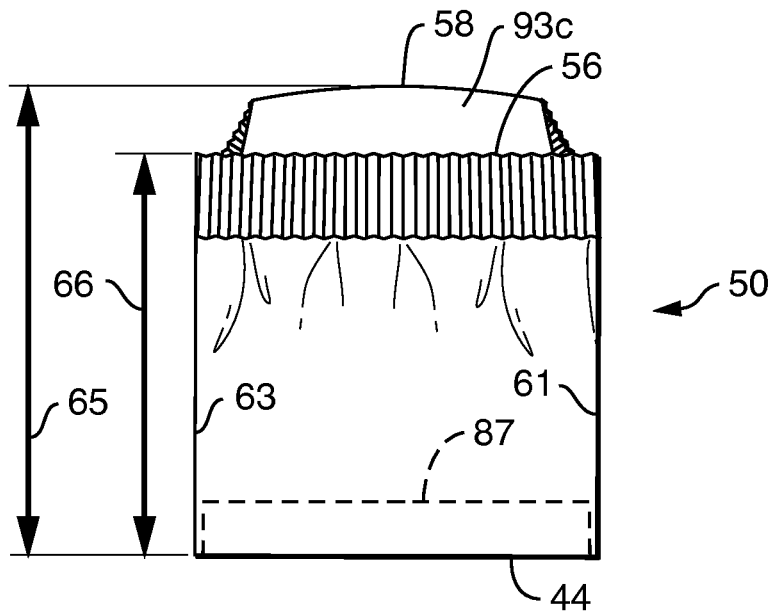
FIG. 4C
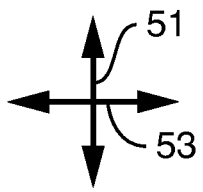
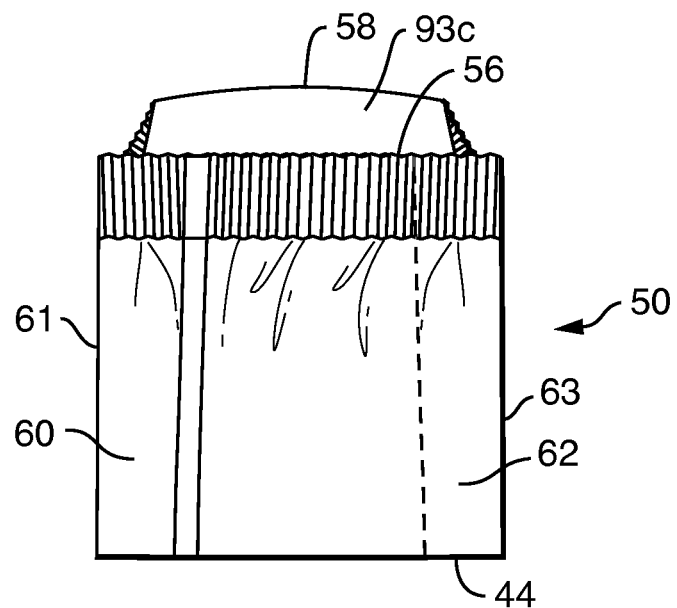
FIG. 4D

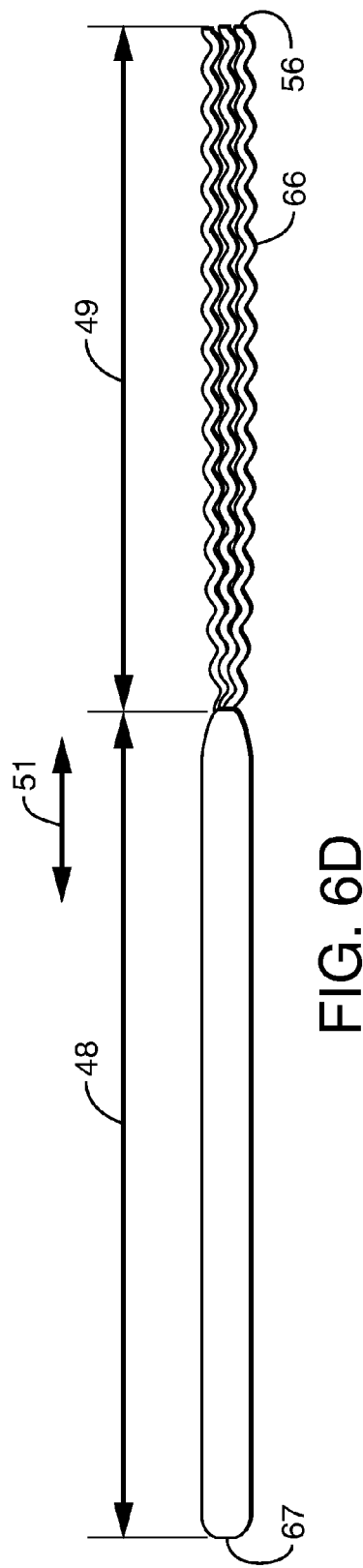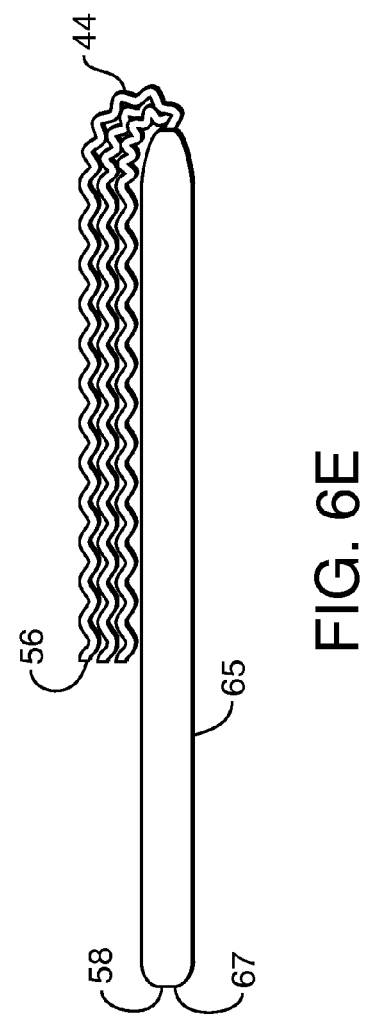
FIG. 6D
FIG. 6E

METHOD OF FOLDING PANT-LIKE DISPOSABLE ABSORBENT GARMENTS IN A TROUGH

BACKGROUND

People rely on disposable absorbent garments in their everyday lives, including such garments as adult incontinence products, enuresis pants, training pants, and diapers. Many manufacturers seek to better meet the needs of users of such products. With certain products, such as adult incontinence underwear and enuresis pants, it is important that the garments look and feel as much as possible like "regular" underwear to promote an improved sense of normalcy to the wearer who suffers from incontinence or enuresis. Additionally, purchasers and users of such products are frequently embarrassed about their condition and about having to purchase products to deal with their incontinence or enuresis condition.

Currently, the most common method for obtaining incontinence and enuresis underwear is by purchasing a plurality of such garments packaged in bags. Typically, the garments are folded in some manner to better fit within the package. Consistent folding of the garments is important for a number of reasons. First, disposable absorbent garments are typically manufactured at a high rate of speed; stacks of folded garments are rapidly and repeatedly pushed into packaging materials, such as flexible plastic bags. Inconsistent folding of the garments can result in bulging or lumpy stacks of folded garments, which can interfere with the automated packaging operation. Second, bulging and lumpy stacks of folded garments result in bulging, uneven filled packages, which can cause the packages to be unstable on retail shelves, as well as appear to the consumer to be suffering in quality. Third, upon removing haphazardly, non-neatly folded garments from the package, consumers may be left with a negative impression of quality. Indeed, poor, unpredictable folding can in some cases impact the performance of the absorbent garment, by creating creases or cracks in the fluid-absorbing core at inopportune locations.

Conventional methods of folding pant-like, disposable absorbent garments are suboptimal. Therefore, what is needed is an improved method of folding pant-like, disposable absorbent garments to promote consistent, predictable, and controlled folding of the garments in high-speed manufacturing processes.

SUMMARY OF THE INVENTION

The present invention relates to a method of folding a pant-like disposable absorbent garment. In one embodiment, the method comprises providing a garment having a waist opening and two leg openings, the garment defining a longitudinal direction and a transverse direction, the garment defining a first waist side region adjacent a first side edge, a second waist side region adjacent a second side edge, a waist center region positioned transversely between the first waist side region and the second waist side region, and a crotch region longitudinally below said waist center region. The garment further includes an absorbent core. The method in this embodiment further includes folding the garment along a transversely extending fold line so as to bring the crotch region into superposed relation with the waist center region; providing a trough, the trough comprising a floor, a first side wall, and a second side wall, the trough defining a trough width extending from the first side wall to the second side wall; placing the waist center region in the trough; and folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the waist center region is in the trough.

In another embodiment, the method defines a machine direction and a cross-machine direction. The method comprises providing a garment having a waist opening and two leg openings, the garment defining a longitudinal direction and a transverse direction, the garment defining a first waist side region adjacent a first side edge, a second waist side region adjacent a second side edge, a waist center region positioned transversely between the first waist side region and the second waist side region, and a crotch region longitudinally below said waist center region. The garment further includes an absorbent core. The method in this embodiment further includes folding the garment along a transversely extending fold line so as to bring the crotch region into superposed relation with the waist center region; transporting the garment in the machine direction, such that the longitudinal direction of the garment is in parallel alignment with the machine direction during the transporting; providing a trough that extends along the machine direction, the trough comprising a floor, a first side wall, and a second side wall, the trough defining a trough width extending along the floor from the first side wall to the second side wall, the trough width extending in a direction parallel to the cross-machine direction; placing the waist center region in the trough; and folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the waist center region is in the trough.

In another embodiment, the method defines a machine direction and a cross-machine direction. The method comprises providing a garment having a waist opening and two leg openings, the garment defining a longitudinal direction and a transverse direction, the garment defining a first waist side region adjacent a first side edge, a second waist side region adjacent a second side edge, a waist center region positioned transversely between the first waist side region and the second waist side region, and a crotch region longitudinally below said waist center region. The garment further includes an absorbent core. The method in this embodiment further includes folding the garment along a transversely extending fold line so as to bring the crotch region into superposed relation with the waist center region; transporting the garment in the machine direction, such that the transverse direction of the garment is in parallel alignment with the machine direction; providing a trough that extends along the cross-machine direction, the trough comprising a floor, a first side wall, and a second side wall, the trough defining a trough width extending along the floor from the first side wall to the second side wall, the trough width extending in a direction parallel to the machine direction, the floor of the trough moving in the machine direction; placing the waist center region in the trough; and folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the waist center region is in the trough.

BRIEF DESCRIPTION OF THE DRAWINGS

FIG. 3A representatively illustrates a front plan view of the disposable absorbent pant of FIG. 2, shown in a relaxed and laid-flat condition.

FIG. 3B representatively illustrates a front plan view of an alternative embodiment of disposable absorbent pant, shown in a relaxed and laid-flat condition FIG. 4A representatively illustrates a front plan view of an intermediate folded configuration of the disposable absorbent pant of FIG. 3, shown in a transversely tensioned condition, with one longitudinal fold.

FIG. 6D is a cross-sectional view of the pant of FIG. 6C as viewed along line 6D-6D.

FIG. 6E is similar to the view of FIG. 6D, but includes one longitudinal fold.

DEFINITIONS

Figure 1:
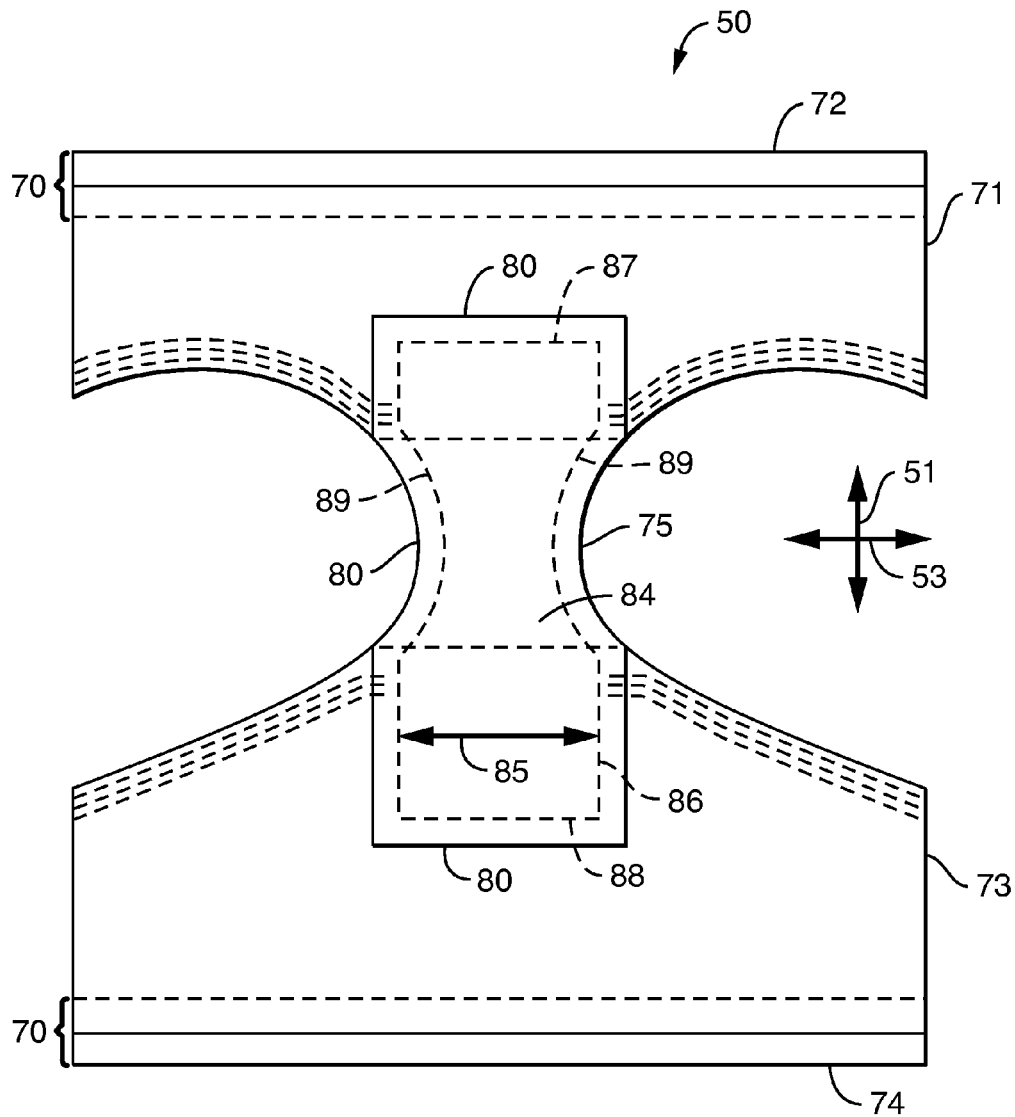
FIG. 1 representatively illustrates a plan view of one embodiment of a disposable absorbent pant suitable for use in conjunction with certain embodiments of the present invention in a longitudinally stretched and laid-flat condition, prior to the joining of the front and back waist regions, and showing the surface of the article that faces the wearer when the article is worn.
Figure 2:
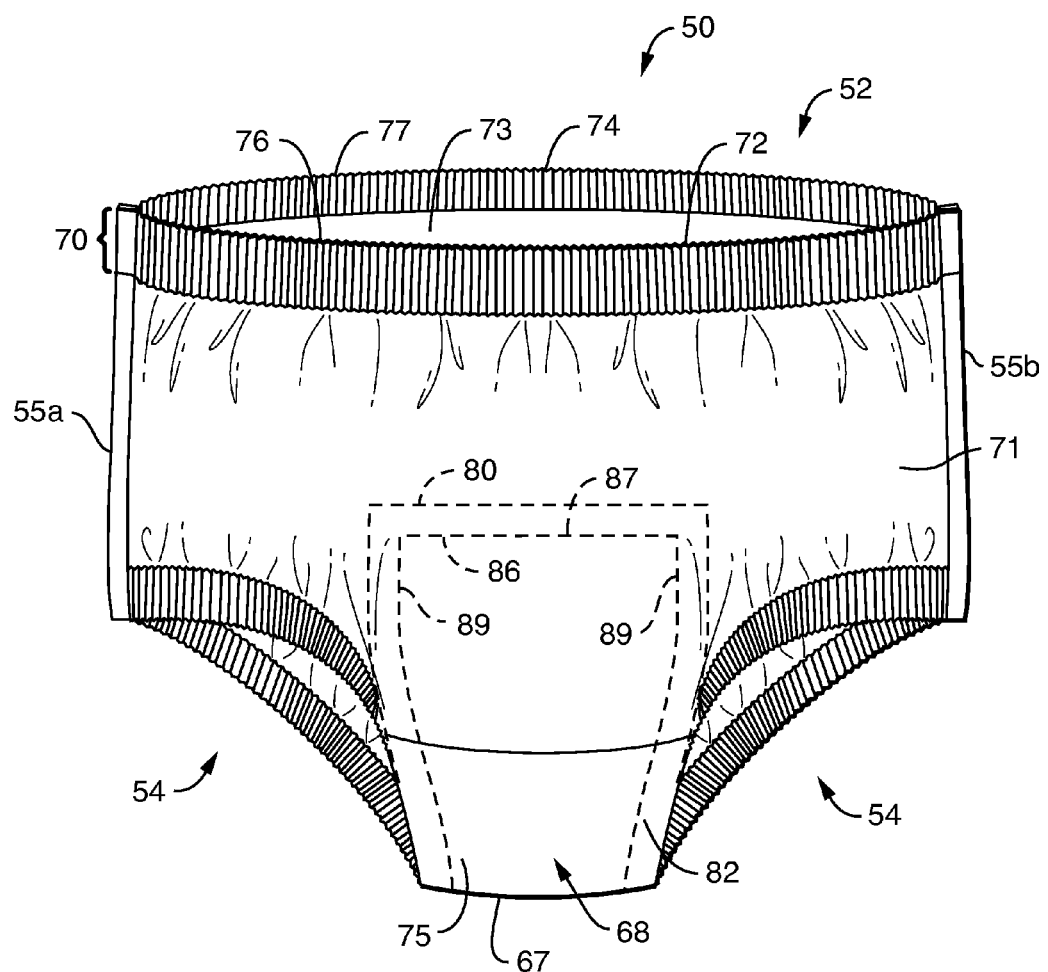
FIG. 2 representatively illustrates a front perspective view of the exemplary embodiment of FIG. 1, shown in a fully assembled condition.
Figure 4A:
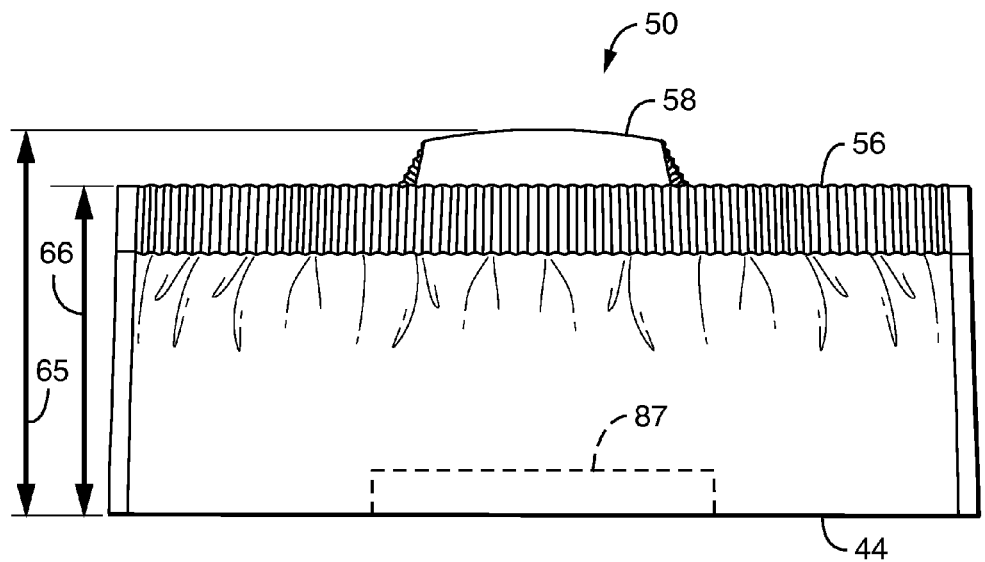
FIG. 4B representatively illustrates a back plan view of an intermediate folded configuration of the disposable absorbent pant of FIG. 3, shown in a transversely tensioned condition, with one longitudinal fold.
FIG. 4C representatively illustrates a front plan view of a fully folded configuration of the disposable absorbent pant of FIG. 3, with both waist side regions folded under the waist center region.
FIG. 4D representatively illustrates a back plan view of a fully folded configuration of the disposable absorbent pant of FIG. 3, with both waist side regions folded over the waist center regions.
Figure 4B:
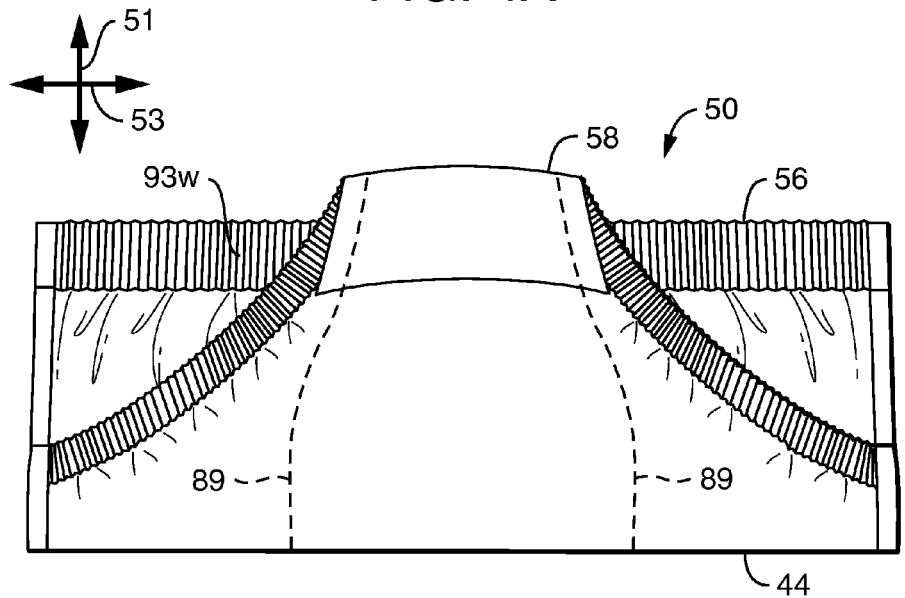
Figure 5A:
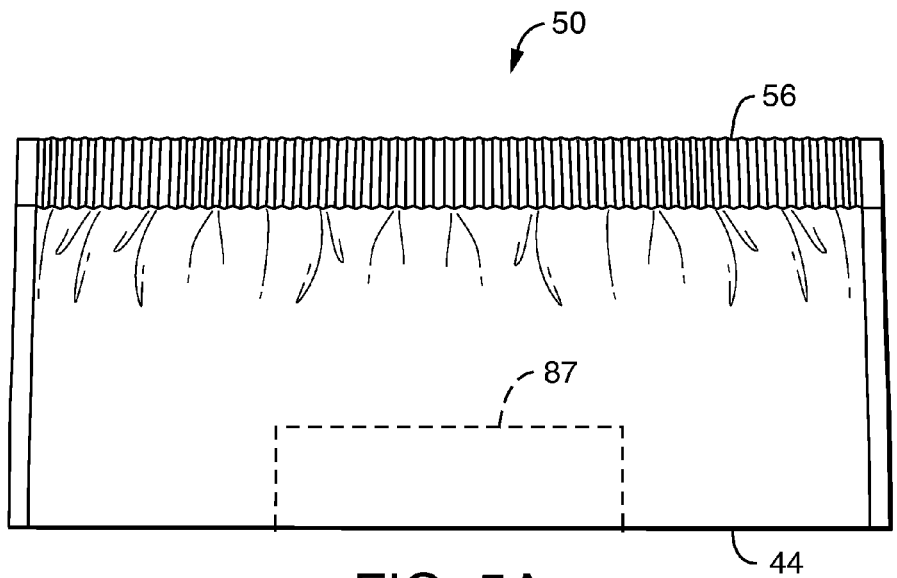
FIG. 5A representatively illustrates a front plan view of an alternative intermediate folded configuration of the disposable absorbent pant of FIG. 3, shown in a transversely tensioned condition, with one longitudinal fold.
Figure 5B:
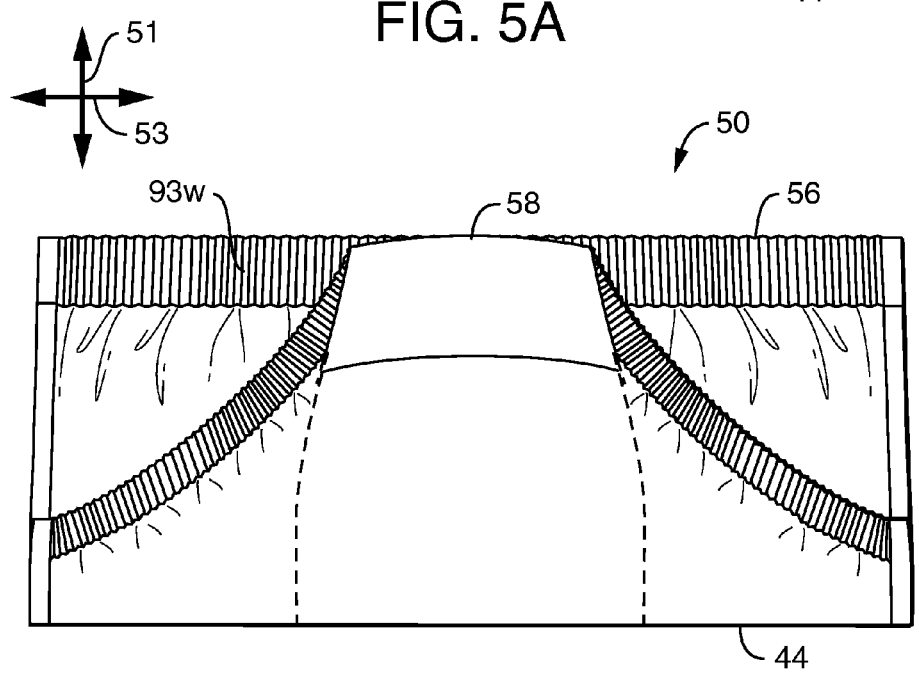
FIG. 5B representatively illustrates a back plan view of an alternative intermediate folded configuration of the disposable absorbent pant of FIG. 3, shown in a transversely tensioned condition, with one longitudinal fold.
Figure 5C:
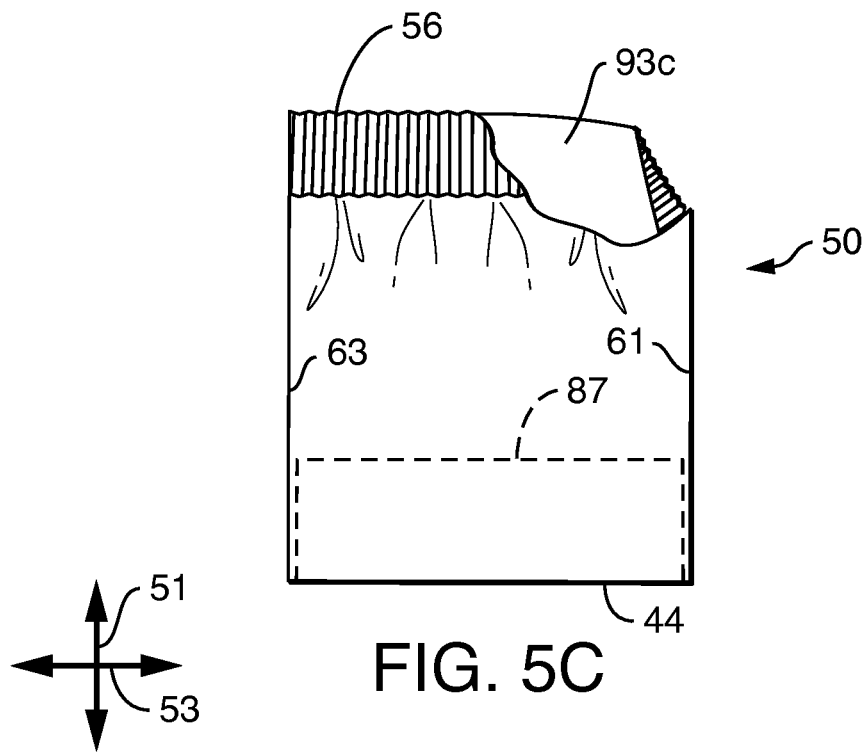
FIG. 5C representatively illustrates a front plan view of an alternative fully folded configuration of the disposable absorbent pant of FIG. 3, with both waist side regions folded under the waist center region, and with portions cut away to show underlying features.
Figure 5D:
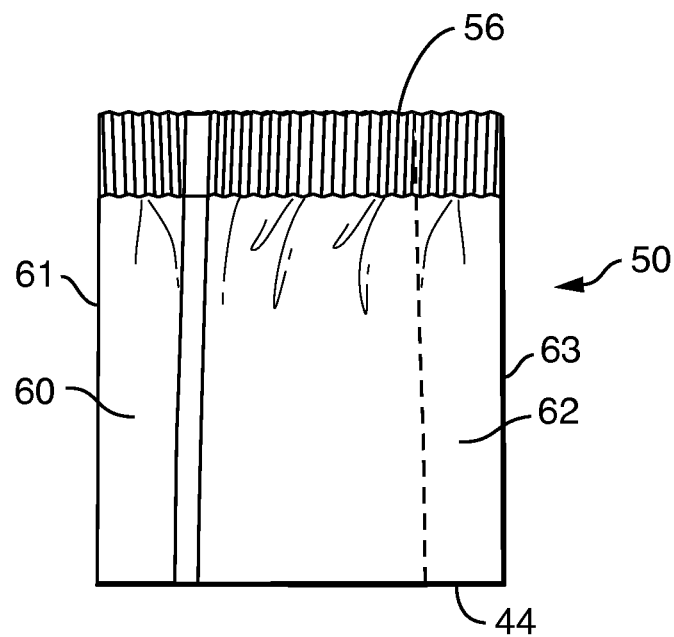
FIG. 5D representatively illustrates a back plan view of an alternative fully folded configuration of the disposable absorbent pant of FIG. 3, with both waist side regions folded over the waist center region.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

"Integral" is used to refer to various portions of a single unitary element rather than separate structures bonded to or placed with or placed near one another.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis.

These terms may be defined with additional language in the remaining portions of the specification.

DETAILED DESCRIPTION OF EXEMPLARY EMBODIMENTS

The present invention relates to a method 20 of folding a pant-like disposable absorbent garment. Reference to the Figures shall be made in describing various embodiments of the invention. It should be noted that the embodiments depicted in the Figures and described herein are merely representative examples of the method of the invention. The various embodiments of the invention are suitable for use in folding disposable absorbent garments such as adult incontinence underwear, prefastened disposable diapers, disposable swim pants, disposable training pants, disposable enuresis garments, and the like. For illustration purposes, various embodiments of the present method invention shall be described in conjunction with the folding of pull-on style incontinence pants.

Figure 6A:
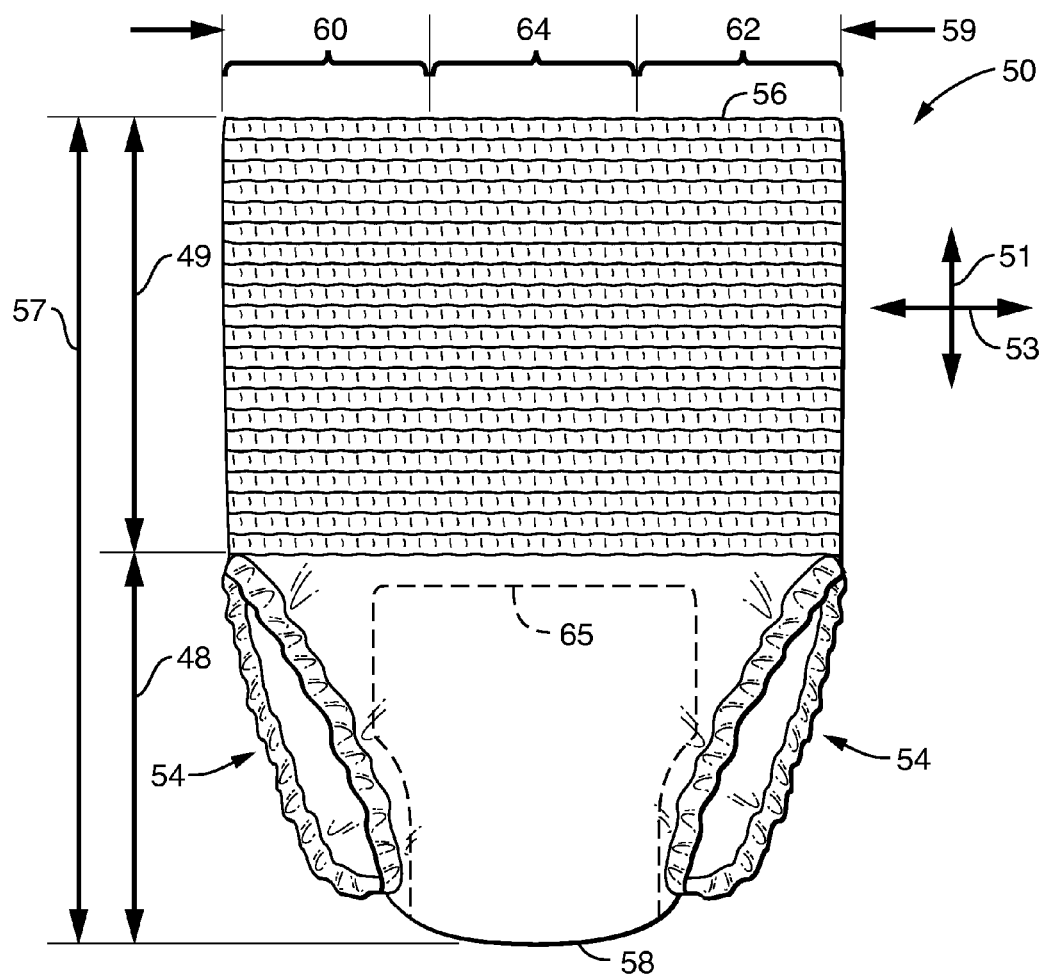
FIG. 6A representatively illustrates a front plan view of an alternative embodiment of a disposable absorbent pant suitable for use in conjunction with certain embodiments of the present invention shown in a relaxed and laid-flat condition.
Figure 6B:
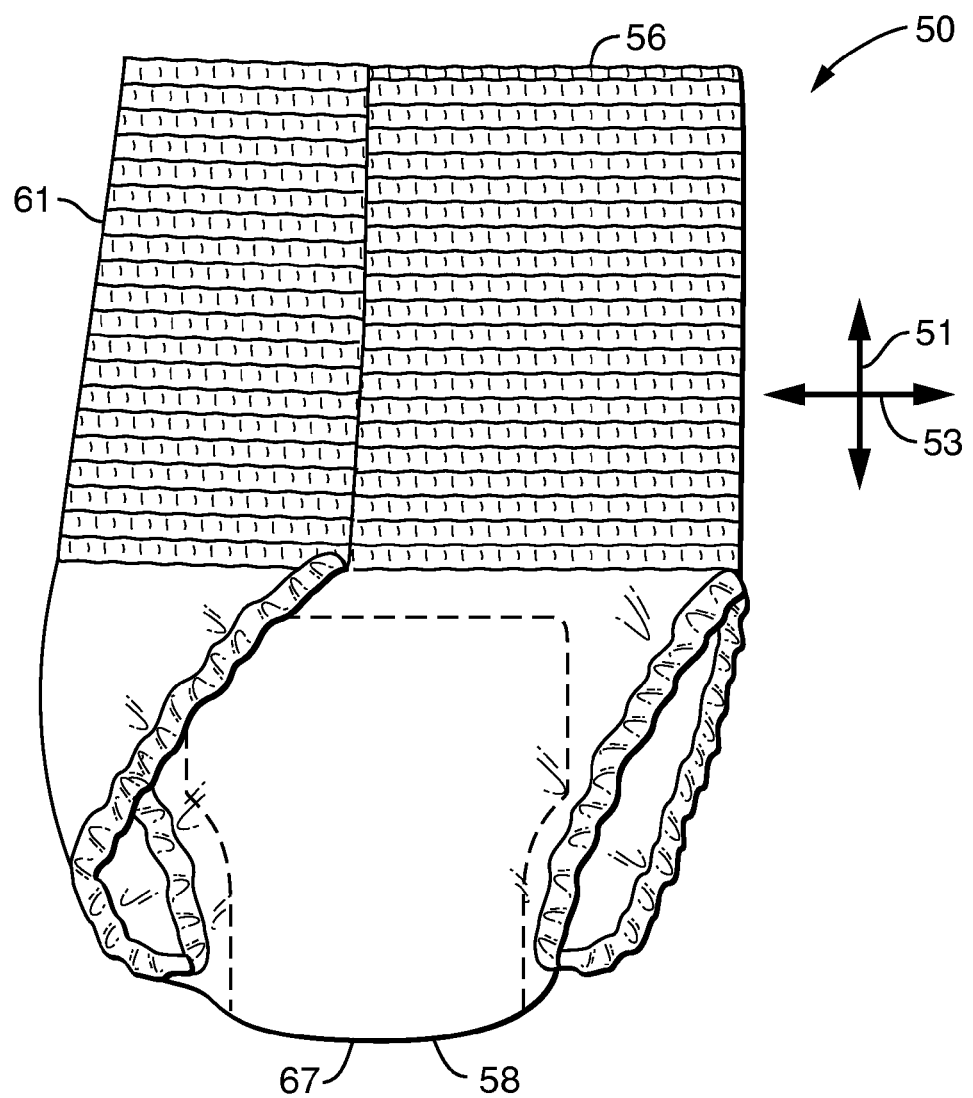
FIG. 6B representatively illustrates a front plan view of the disposable absorbent pant of FIG. 6A, shown in a relaxed and laid-flat condition, with one waist side region folded over the waist center region.
Figure 6C:
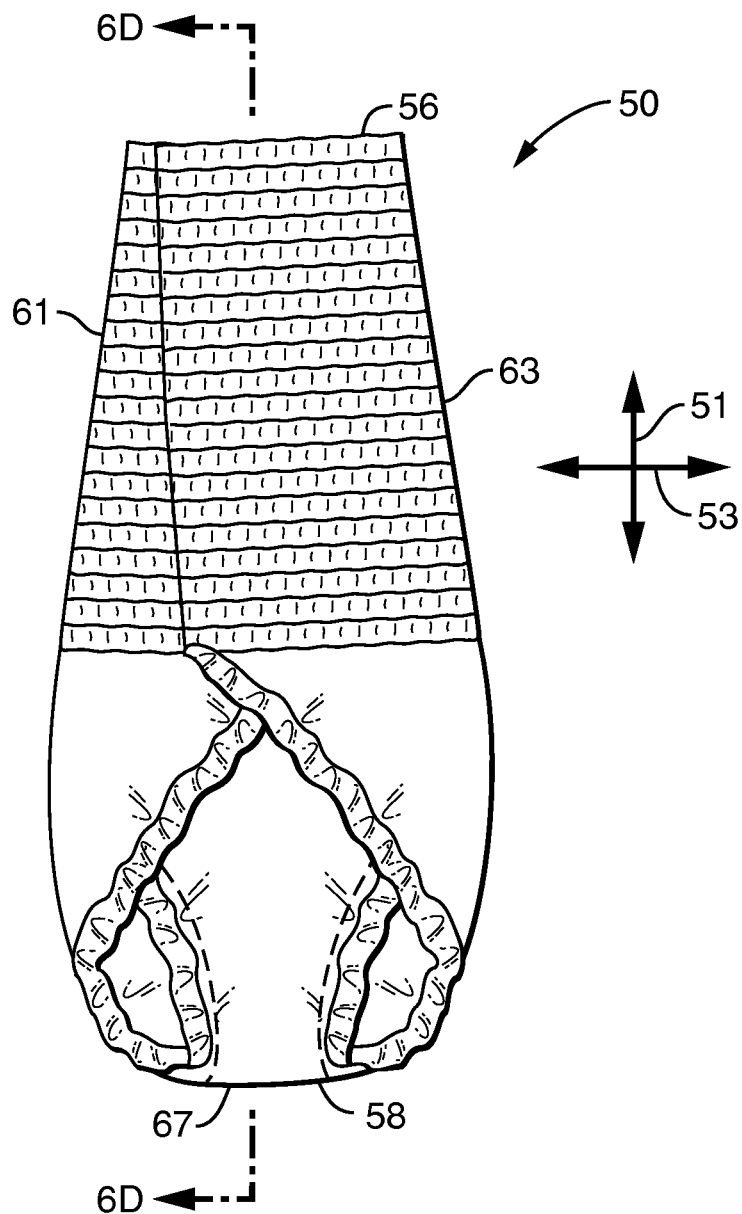
FIG. 6C representatively illustrates a front plan view of the disposable absorbent pant of FIG. 6A, shown in a relaxed and laid-flat condition, with both waist side regions folded over the waist center region.

In particular embodiments, each garment or pant 50 defines a waist opening 52, two leg openings 54, a waist end 56, a crotch end 58, and first and second side edges 55a, 55b. In particular embodiments, each pant includes a pair of side seams 91, 91 which join the front portion of the pant to the back portion. Each pant can include a crotch fold 67. Each pant defines a longitudinal direction 51 that extends from the waist end 56 to the crotch end 58, and each pant defines a transverse direction 53 that is perpendicular to the longitudinal direction 51. Each pant 50 defines an assembled length 57 which extends in the longitudinal direction 51 from the waist end 56 to the crotch end 58. (If the front waistband portion 72 and the back waistband portion 74 are different distances from the crotch end 58, then the assembled length 57 of the pant is the longer of the two distances.) Each pant also defines a width 59 which extends in the transverse direction 53 from one side edge 55a to the other side edge 55b. The length 57 and width 59 for purposes herein are measured when the pant is in a fully assembled (side seams intact), relaxed condition, such as that depicted in FIG. 3. The length 57 is measured at the longitudinal centerline of the pant 50, and the width 59 is measured at the longitudinal midpoint of each side seam 55. Each pant further defines a first waist side region 60, a second waist side region 62, and a waist center region 64 positioned transversely between the first waist side region 60 and the second waist side region 62. The first waist side region 60 extends approximately 20% to 40% of the transverse width 59 of the pant 50 in an assembled, laid-flat, relaxed condition. The second waist side region 62 extends approximately 20% to 40% of the transverse width 59 of the pant 50 in an assembled, laid-flat, relaxed condition. The waist center region 64 extends approximately 20% to 60% of the width 59 of the pant 50 in an assembled, laid-flat, relaxed condition. In particular embodiments, the first waist side region 60, the second waist side region 62, and the waist center region 64 each extend approximately one-third of the width 59 of the pant 50 in a laid-flat, relaxed condition, as is generally representatively illustrated in FIG. 3. Each waist region 60, 62, 64 extends in the longitudinal direction 51 generally from the waist end 56 to the top of the leg openings 54, 54, as indicated by the arrows 49 in FIGS. 3A and 6A.

In particular embodiments, each pant includes a front panel 71, a back panel 73, and a crotch panel 75. The panels 71,73,75 may be integral with each other, or may comprise separate components attached to one another. In particular embodiments, the front and back panels 71,73 comprise elastomeric materials, such as elastomeric film laminates, elastomeric stranded laminates, elastomeric net or mesh laminates, or the like. In one example, the front and back panels 71,73 each comprise an elastomeric film sandwiched between two polyolefin-based, cloth-like, nonwoven substrates.

Each pant 50 further defines a waistband region 70 which abuts the waist end 56. The waistband region 70 extends in the transverse direction 53 and at least partially encircles the waist opening 52. Each waistband region 70 comprises a front waistband portion 72 and a back waistband portion 74. Each waistband portion 72,74 extends between the side seams 55. The front waistband portion 72 is adapted to contact the front half of a wearer's waist when donned, and the back waistband portion 74 is adapted to contact to the back half of a wearer's waist when donned. The waistband portions 72,74 can be integral with the front and back panels 71,73, or can be separate components that are attached to the front and back panels 71,73. For example, the front waistband portion 72 can constitute the region of the front panel 71 that is within 25 centimeters, or within 35 centimeters, of the front waist edge 76, and the back waistband portion 74 can constitute the region of the back panel 73 that is within 25 centimeters, or within 35 centimeters, of the back waist edge 77. Alternatively, the front waistband portion 72 can comprise a folded-over portion of the front panel 71, and/or the back waistband portion 74 can comprise a folded-over portion of the back panel 73. In particular embodiments, a transversely extending fold line defines the front waist edge 76, and a transversely extending fold line defines the back waist edge 77. In such embodiments, the longitudinal length of the folded portion defines the boundaries of the respective waistband portion. Desirably, one or more elastic strands are disposed within one or both folded-over portions. Examples of particular embodiments of such folded-over waistband configurations are shown in U.S. Patent Application Publication 2008/0134487 to Hartono, which is incorporated by reference to the extent consistent herewith. Alternatively, the front waistband portion 72 can comprise a separate elastomeric component or assembly affixed to the front panel 71, and/or the back waistband portion 74 can comprise a separate elastomeric component or assembly affixed to the back panel 73, as representatively illustrated in FIG. 1. Each pant also defines a crotch region 68 which abuts the crotch end 58. The crotch region 68 extends in the longitudinal direction 51 generally from the crotch end 58 to the tops of the leg openings 54, 54, as indicated by the arrows 48 in FIGS. 3A and 6A.

Each pant also desirably includes an absorbent composite 80 generally disposed in the waist center region 64 and in the crotch region 68. In particular embodiments, the absorbent composite 80 can include a liquid-impermeable garment-side backsheet 82, a liquid-permeable body-side top sheet 84, and a fluid-absorbing core 86 comprised of fluff pulp and/or superabsorbent polymer sandwiched between the backsheet 82 and the top sheet 84. The absorbent core 86 has a front edge 87, a back edge 88 spaced from the front edge in the longitudinal direction, and two side edges 89 which extend longitudinally from the front edge 87 to the back edge 88. The absorbent core 86 may be rectangular, hourglass, oval, trapezoid, or other suitable shape. Due to the additional bulk introduced by an absorbent core 86, the regions of a pant 50 that include an absorbent core 86 is generally thicker than other regions of such pant. Examples of disposable absorbent pants suitable for use in conjunction with the method of the present invention include those disclosed in U.S. Pat. No. 5,745,922 issued May 5, 1998 to Rajala et al., U.S. Pat. No. 6,240,569 issued Jun. 5, 2001 to Van Gompel et al., U.S. Pat. No. 6,702,798 issued Mar. 9, 2004 to Christoffel et al., and U.S. Pat. No. 7,604,624 issued Oct. 20, 2009 to Veith et al., the contents of each of which is hereby incorporated by reference to the extent consistent herewith. Note that the disposable absorbent pants could be provided in a permanently "closed" (i.e., pull-on style) configuration, a releasably and refastenably "closed" configuration, or an "open" (i.e., non-prefastened) configuration—any of which could be used in conjunction with the various embodiments of the present invention.

In particular embodiments, the method 20 includes folding each pant at least once in the longitudinal direction 51. In particular embodiments, as representatively illustrated in FIGS. 4-5, the pant 50 is folded at a transversely extending fold line 44 so as to bring the crotch region 68 into superposed relation (and optionally contacting relation) with the waist center region 64. The crotch end 58 can be positioned to be flush with the waist end 56, as representatively illustrated in FIGS. 5A-D. Alternatively, the crotch end 58 can be positioned to not be flush with the waist end 56, such that the waist end 56 and the crotch end 58 are different distances from the fold line 44. For example, as depicted in FIGS. 4A-D, the pant 50 may be folded such that distance 65 between the crotch end 58 and the fold line 44 is greater than the distance 66 between the waist end 56 and the fold line 44. The first longitudinal fold line 44 can be, but need not be, longitudinally near the front edge 87 of the absorbent core 86, as is the case in the embodiment of FIG. 4. The pant may be folded at fold line 44 such that the crotch region 68 is brought into superposed relation with the front panel 71, or with the back panel 73. In particular embodiments, such as that representatively illustrated in FIGS. 4 and 5, the pant 50 is folded such that the crotch region 68 at least partially directly contacts the back waistband portion 74. In such an embodiment, the garment-side surface 93c of the crotch region 68 of the pant 50 directly contacts the garment side-surface 93w of the back waistband portion 74 of the waistband region 70.

Referring to FIGS. 8, 9, and 11-13, the method 20 further includes providing a trough 100. The trough comprises a floor 102, a first side wall 104, and a second side wall 106. The trough defines a trough width 105, which as used herein refers to the distance extending from the bottom of the first side wall 104 to the bottom of the second side wall 106 (that is, along the floor 102). If the trough width varies along the length of the trough 100, then the trough width as used herein refers to the narrowest trough width along the length of the trough 100. The trough also defines a trough maximum depth, defined as the maximum distance between the floor 102 and an imaginary plane occupied by the top edges of the first and second side walls 104, 106. The side walls 104, 106 can be perpendicular to the floor 102, or one or both of the side walls 104, 106 could be positioned at an oblique angle to the floor 102.

Referring to FIGS. 8 and 11-13, the method further comprises placing the waist center region 64 of the garment 50 in the trough 100. In particular embodiments, the crotch region 68 of the garment 50 is also placed in the trough, as is representatively illustrated in FIGS. 8 and 12. After the waist center region 64, and preferably also the crotch region 68, have been placed in the trough 100, the method further includes folding the garment 50 at least once, and preferably twice, in the transverse direction 53. FIGS. 8 and 11-13 show garments 50 in various stages of folding while in a trough 100. FIGS. 10 and 14 depict various stages of folding that can be accomplished using a trough, but with the actual trough and associated apparatus removed to more clearly depict the various folding stages. In particular embodiments, as representatively illustrated in FIGS. 8-14, the first waist side region 60 and the second waist side region 62 of each pant 50 are folded over, or moved into superposed relation with, the waist center region 64. For example, the method can include folding the garment 50 along a longitudinally extending first fold line 61 so as to position the first waist side region 60 over the waist center region 64. Preferably, the first fold line 61 is adjacent the first side wall 104. Similarly, the method can include folding the garment 50 along a longitudinally extending second fold line 63 so as to position the second waist side region 62 over the waist center region 64. Preferably, the second fold line 63 is adjacent the second side wall 106. In particular embodiments, the first waist side region 60 is folded over the waist center region 64, and the second waist side region 62 is folded over both the waist center region 64 as well as the first waist side region 60. In this way, the pant 50 is in particular embodiments folded twice in the transverse direction 53.

Figure 7A:
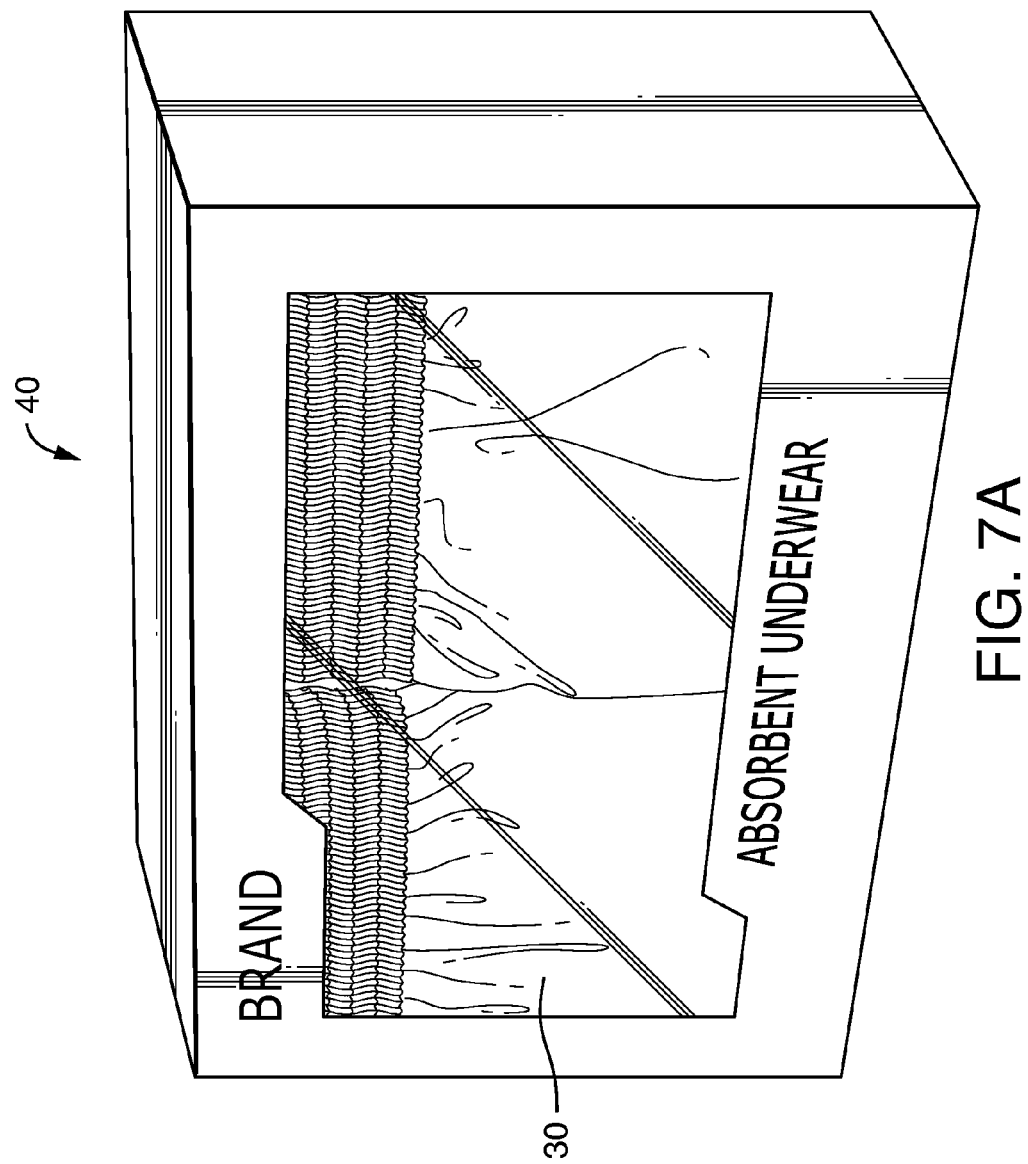
FIG. 7A representatively illustrates a perspective view of one embodiment of a package of disposable absorbent garments folded using particular embodiments of the present invention.
Figure 7B:
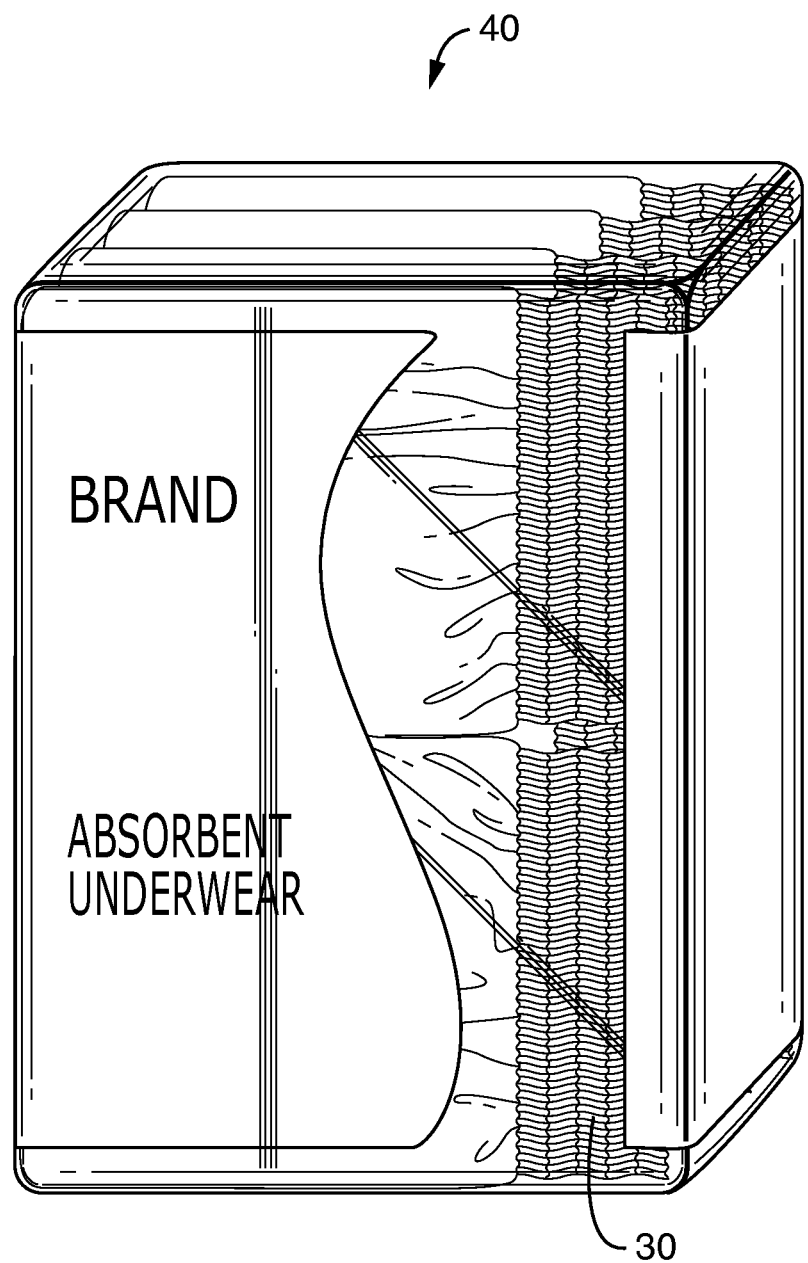
FIG. 7B representatively illustrates a perspective view of an alternative embodiment of a package of disposable absorbent garments folded using particular embodiments of the present invention.

As set forth earlier, the method preferably includes folding each pant at least once in the longitudinal direction 51, such as at a transversely extending fold line 44, to bring the crotch region 68 into superposed relation with the waist center region 64. In particular embodiments, folding of the garment along the transversely extending fold line 44 occurs before folding of the garment along the first and second fold lines 61, 63. Examples of this approach are representatively illustrated in FIGS. 10B and 14. Stated another way, in particular embodiments, the pant 50 is folded at least once in the longitudinal direction 51 so as to position the crotch end 58 in close proximity to the waist end 56 before the pant 50 is folded in the transverse direction 53. For example, as representatively illustrated in the embodiment of FIGS. 4 and 5, the pant 50 is first folded at a transversely extending fold line 44, is thereafter folded at a longitudinally extending first fold line 61, and is finally folded at a longitudinally extending second fold line 63. In the folded configuration depicted in FIG. 5, the majority of the crotch region 68 is at least partially sandwiched between the first waist side region 60 and the center waist region 64. In particular embodiments, such as that representatively illustrated in FIG. 5, both the front waistband portion 72 and the back waistband portion 74 of the waistband region 70 are wrapped around the crotch region 68. In such embodiments, it can be desirable to have the waistband region 70 of the pant in a tensioned condition. Having the waistband region 70 in a tensioned or partially taut condition can assist in highlighting the "real underwear"-like properties of the pant to a consumer viewing the pant, such as through a transparent window region 30 of a package 40, as shown in FIGS. 7A and 7B.

In other embodiments, folding of the garment along the transversely extending fold line 44 occurs after folding of the garment along the first and second fold lines 61, 63. Examples of this approach are representatively illustrated in FIGS. 6A-E and 10A. The first waist side region 60 and the second waist side region 62 of each pant 50 are first folded over, or moved into superposed relation with, the waist center region 64. Thereafter, the garment is folded at the transversely extending fold line 44 so as to bring the crotch region 68 into superposed relation with the waist center region 64.

Referring to FIGS. 1 and 3B, in particular embodiments, the absorbent core 86 defines a maximum core width 85. "Maximum core width" as used herein means the longest transverse distance between the first and second core side edges 89, 89. In particular embodiments, such as that representatively illustrated in FIG. 3B, the maximum core width 85 exceeds the trough width 105, such that the first fold line 61 and the second fold line 62 each extend into the absorbent core 86. In particular embodiments, the method of the present invention can deliver consistent, robust folds of the waist side regions 60, 62, despite the presence of relatively thick and bulky absorbent core "ears" in the territory of the fold lines 61, 63.

The method 20 defines a machine direction 22 and a cross-machine direction 24 that is perpendicular to the machine direction. "Machine direction" is understood by those of skill in the art, and means the primary direction of travel of product webs or work pieces in a manufacturing process, or in a segment of a manufacturing process.

Figure 8:
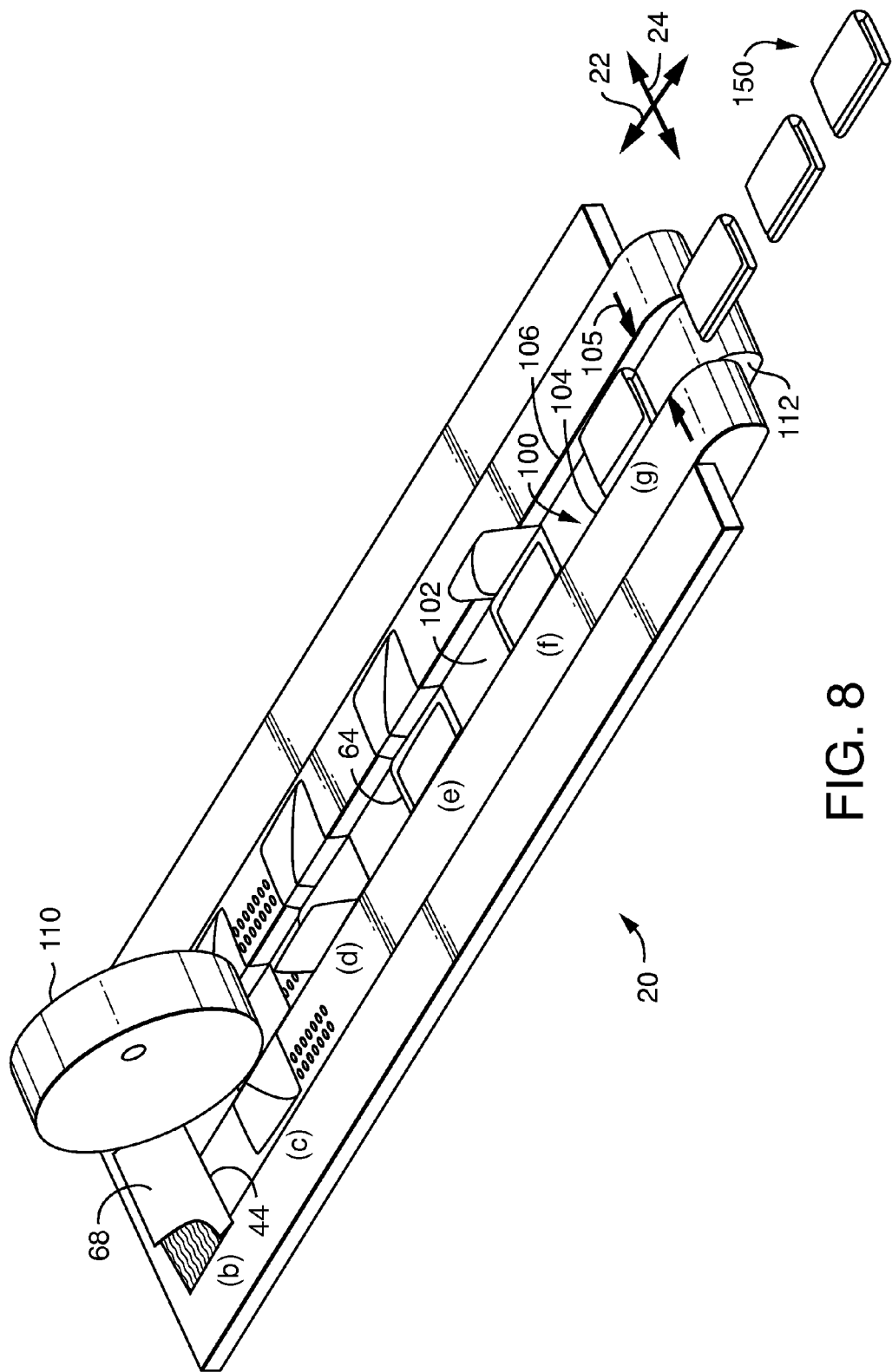
FIG. 8 representatively illustrates a perspective view of one embodiment of the method of the present invention.
Figure 9:
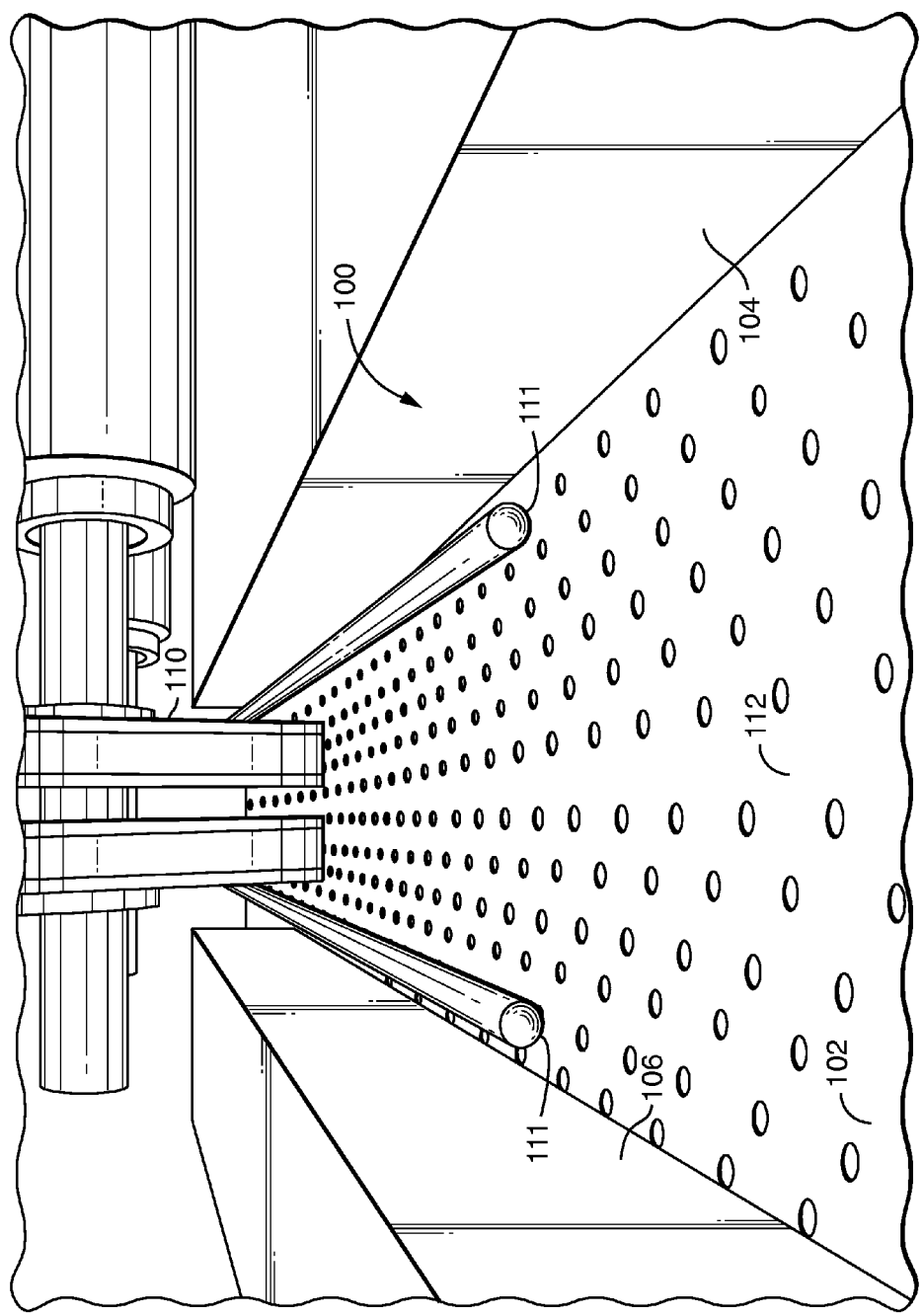
FIG. 9 representatively illustrates a perspective view of one embodiment of a portion of an apparatus suitable for use in conjunction with particular embodiments of the method of the present invention.
Figure 10A:
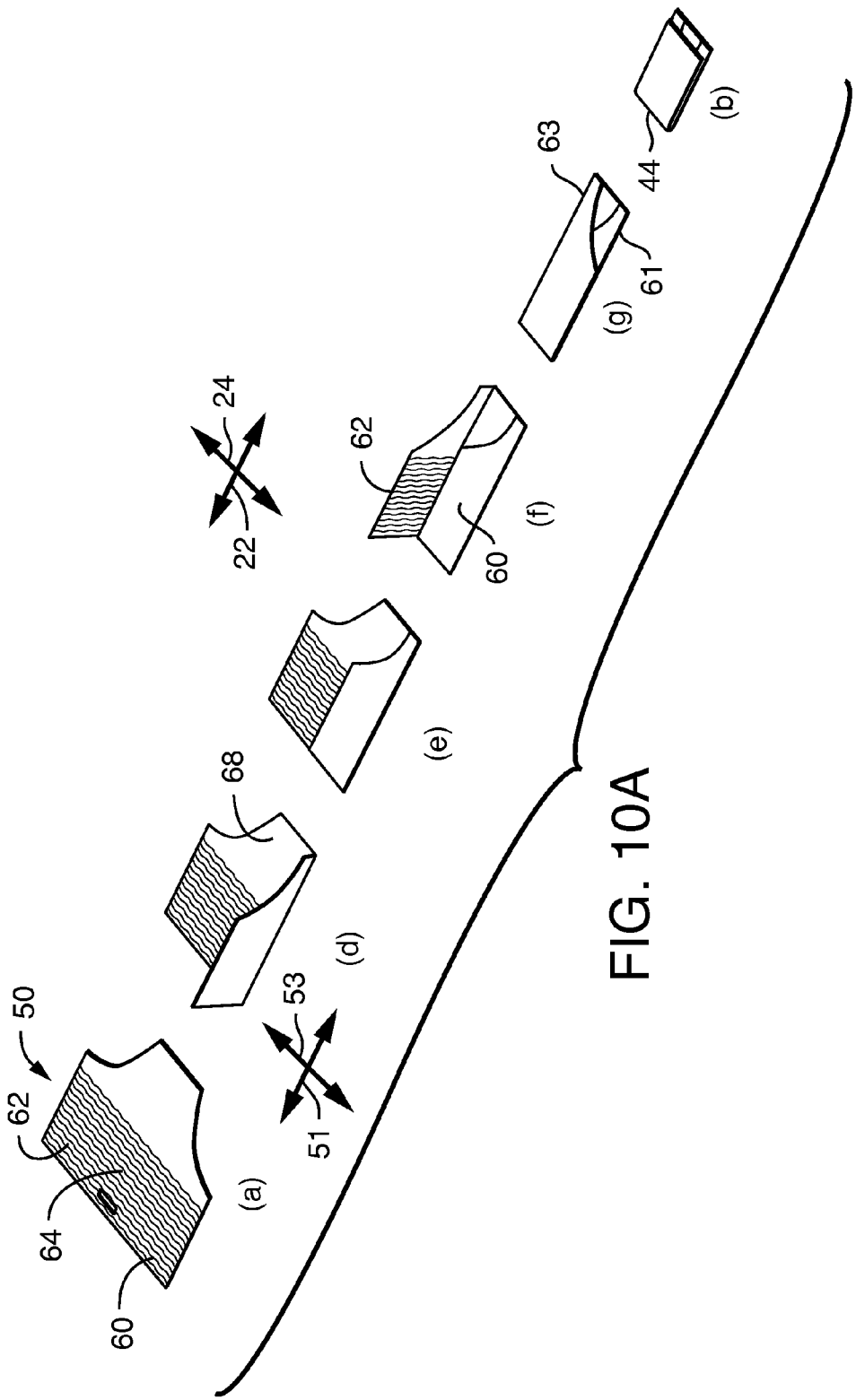
FIG. 10A representatively illustrates a perspective view of various stages of folding a garment in general accordance with the exemplary embodiment of FIG. 8, with a change made to the order of the folding steps.
Figure 10B:
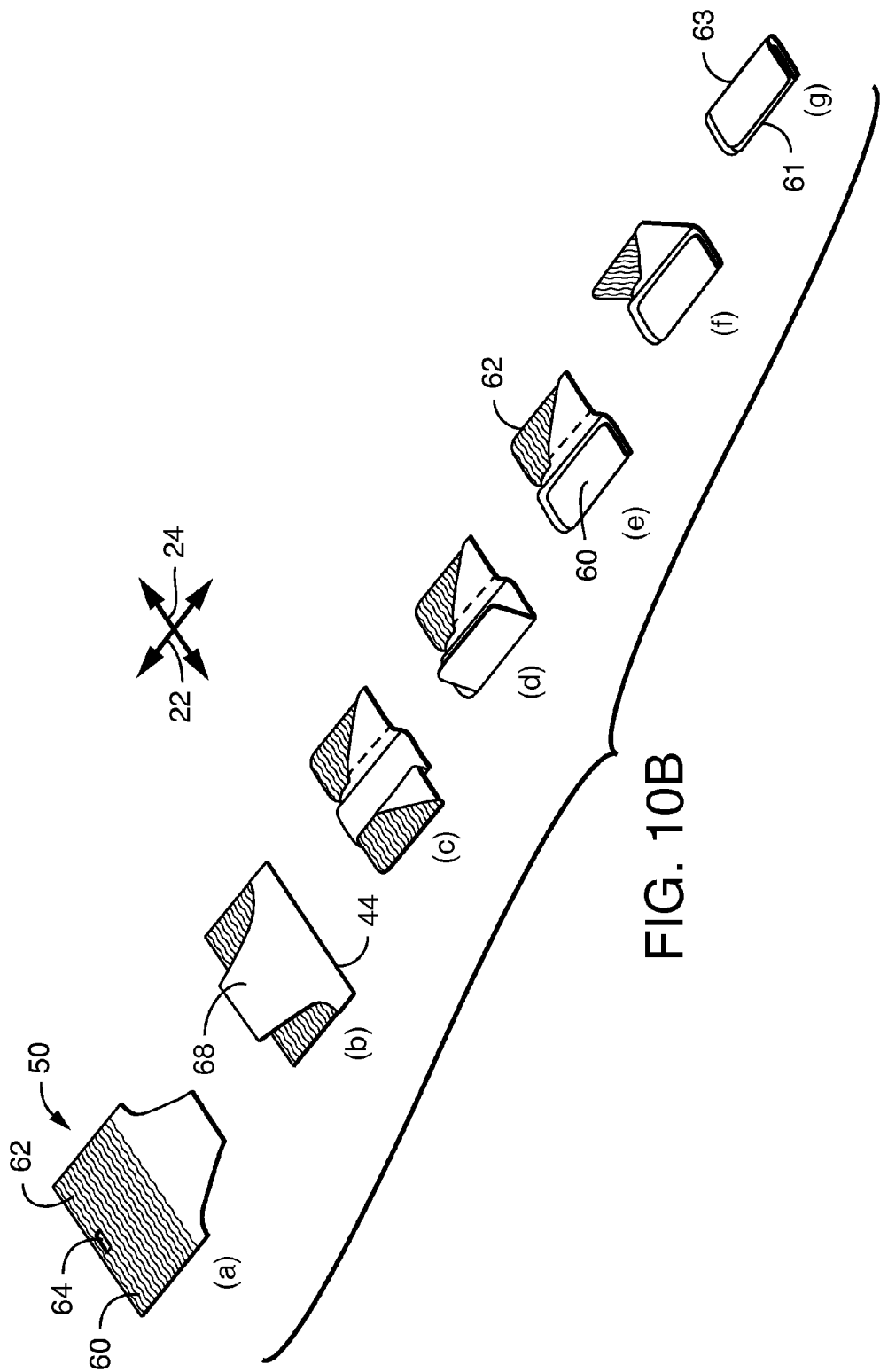
FIG. 10B representatively illustrates a perspective view of various stages of folding a garment in general accordance with the exemplary embodiments of FIG. 8.

Referring to FIGS. 8-10, in particular embodiments, the method 20 includes transporting each garment 50 in the machine direction 22, such that the longitudinal direction 51 of each garment 50 is in parallel alignment with the machine direction 22 during the machine-direction transport. In such embodiments, the trough 100 preferably extends along the machine direction 22, such that the trough side walls 104, 106 extend in the machine direction 22 and such that the trough width 105 extends in the cross-machine direction 24. FIGS. 8-10 representatively illustrate stages of garment folding in such an embodiment. In step (a), the pant-like garment 50 exists in an unfolded, laid-flat condition, such as a relaxed, unfolded, laid-flat condition. In step (b), the garment 50 has been folded at the transversely extending fold line 44 so as to bring the crotch region 68 into superposed and contacting relation with the waist center region 64. In step (c), the waist center region 64 and the crotch region 68 of the garment 50 are placed in, and optionally pressed into, the trough 100. In steps (d) and (e), the garment 50 is folded along a longitudinally extending first fold line 61 so as to position the first waist side region 60 over the waist center region 64. The first fold line 61 is adjacent the first side wall 104. In steps (f) and (g), the garment 50 is folded along a longitudinally extending second fold line 63 so as to position the second waist side region 62 over the waist center region 64. The second fold line 63 is adjacent the second side wall 106. After the garment 50 is thus folded twice in the transverse direction 53, the garment in particular embodiments exits the trough 100. In particular embodiments, the fully folded garment 80 exits the trough directly into a stacker (not shown). Note that step (b) can either occur before steps (d)-(g) (e.g., FIG. 10B) or after steps (d)-(g) (e.g., FIG. 10A).

In particular embodiments, the floor 102 of the trough 100 moves in the machine direction 22. One example of such a configuration is a conveyor 112 as employed in the configuration of FIGS. 8 and 9. Preferably, the floor 102 of the trough 100 extends in a flat plane, as is the case in the embodiments of FIGS. 8 and 9. Alternatively, the floor of the trough can define a curved plane, such as if the trough extends circumferentially around a large drum that rotates in the machine direction.

In particular embodiments, the first side wall 104 comprises a first side conveyor, and the second side wall 106 comprises a second side conveyer. In such an embodiment, the first and second side conveyors can act to transport the garment in the machine direction. In particular embodiments in which the side walls comprise side conveyors, the floor 102 comprises a floor conveyer, and the first side conveyor, the second side conveyor, and the floor conveyor advance together in the machine direction 22. In other embodiments, both the first and second side walls 104, 106 are stationary. In certain embodiments, both the first and second side walls 104, 106 comprise vacuum holes through which vacuum forces are imparted, and the vacuum forces attract the garment to the first and second side walls 104, 106.

In particular embodiments, placing the garment 50 in the trough 100 comprises pressing the waist center region 64 (and optionally the crotch region 68) against the floor 102 of the trough 100 using a pressing mechanism 110, such that the garment is compressedly sandwiched between the floor 102 and the pressing mechanism 110. The pressing mechanism 110 can comprise, for example, a wheel, a belt conveyor, one or more sets of cables and pulleys, a flat plat, a compressed stream of air, or the like.

In particular embodiments, the method further includes restraining the garment 50 in the trough 100 using one or more restraining members 111, 111. For example, as representatively illustrated in FIG. 9, a pair of restraining members 111, 111 in the form of elongated rods are present. The restraining member or members 111, 111 act to restrain the garment 50 in the trough during at least part of the folding step or steps. In the embodiment of FIG. 9, the rods assist in keeping the waist center region 64 and the crotch region 68 securely pressed against the floor 102 in the "corner" regions where the floor 102 meets the side walls 104, 106.

Figure 15:
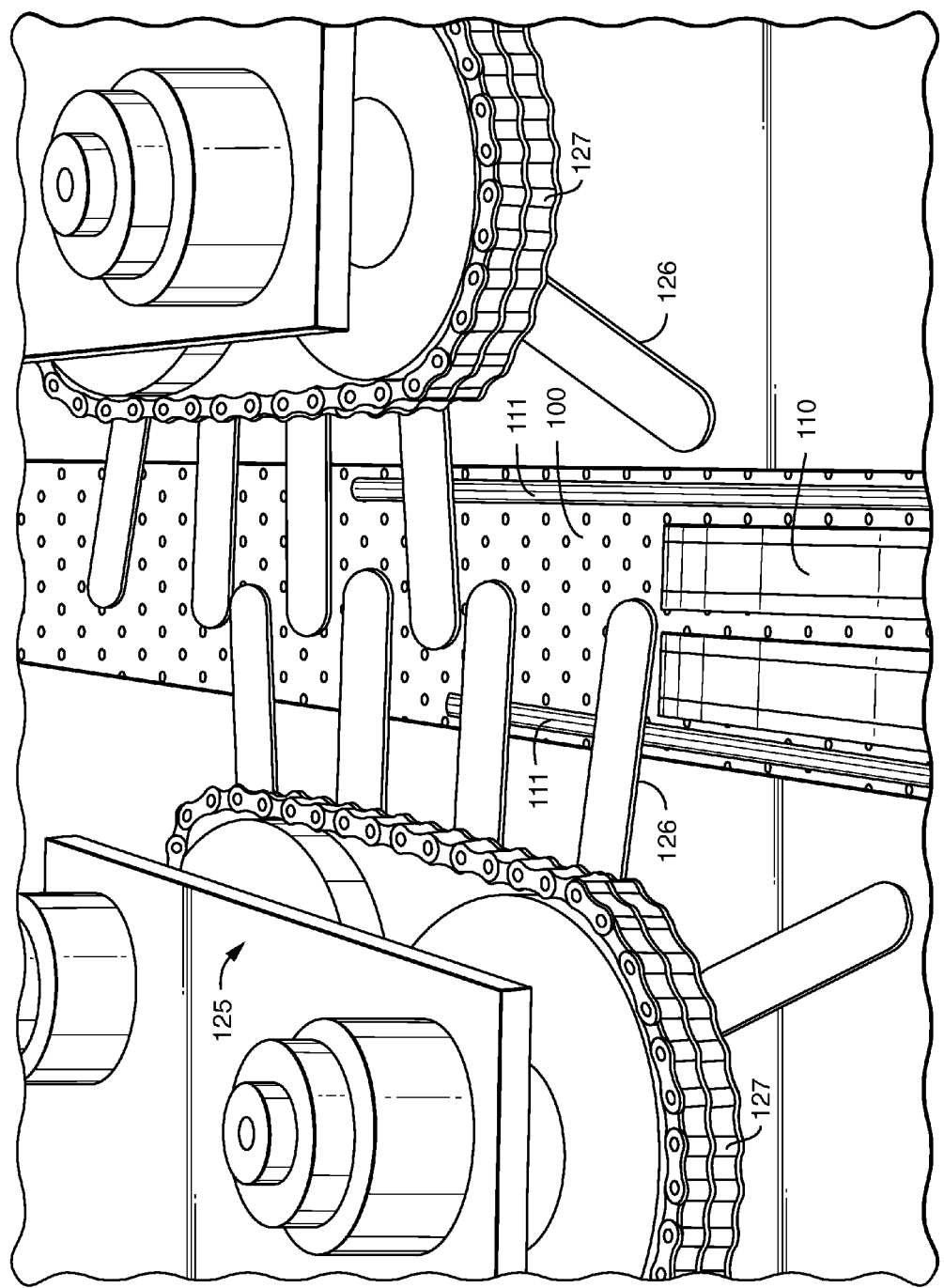
FIG. 15 representatively illustrates a top perspective view of one embodiment of a portion of an apparatus suitable for use in conjunction with embodiments of the invention such as that illustrated in FIG. 8.

The transverse folding of the first and second waist side regions 60, 62 can be accomplished by any of a variety of techniques. For example, folding the garment along the first and second fold lines can be accomplished via twist conveyor belt. In such an approach, each waist side region is manipulated by one or two twist conveyor belts, whereby each belt or set of belts twists approximately 180 degrees as they extend in the machine direction. In another example, folding the garment along the first and second fold lines is accomplished via a pair of elongated vacuum chutes. In such an approach, each waist side region is manipulated by virtue of being drawn into vacuum chutes that extend in the machine direction, the chutes being contoured or twisted in such a manner as to accomplish the folding step. In another example, folding the garment along the first and second fold lines is accomplished via a pair of stationary folding boards or plates. In such an approach, left and right plates extend in the machine direction, and gradually angle inwardly from the regions near the trough walls toward a machine-direction centerline of the trough. As the plates angle inwardly, and as the garment is transported in the machine direction between the plates, the angled edges of the plates move the waist side regions 60, 62 so that they become folded over the waist center region 64. In yet another example, representatively illustrated in FIG. 15, folding the garment along the first and second fold lines is accomplished via a pair of rotary or belt- or chain-link-type blade modules 125. In such an approach, plates, blades, or fingers 126 are mounted to a rotating shaft, a belt, a chain link 127, or the like. The motion of the blades of fingers 126 is configured to make contact with the waist side regions 60, 62, and to fold the waist side regions 60, 62 over the waist center region 64.

Referring to FIGS. 11-14, in particular embodiments the method 20 includes transporting the garments 50 in the machine direction 22, such that the transverse direction 53 of each garment 50 is in parallel alignment with the machine direction 22 during the machine-direction transport. In such embodiments, the trough 100 preferably extends along the cross-machine direction 24, such that the trough side walls 104, 106 extend in the cross-machine direction 24 and such that the trough width 105 extends in the machine direction 22. FIGS. 11-14 representatively illustrate stages of garment folding in such an embodiment. In step (a), the pant-like garment 50 exists in an unfolded, laid-flat condition; the garment could be stretched under tension at this stage, or relatively relaxed. In step (b), the garment 50 has been folded at the transversely extending fold line 44 so as to bring the crotch region 68 into superposed and contacting relation with the waist center region 64. In step (c), the waist center region 64 and the crotch region 68 of the garment 50 are placed in, and optionally pressed into, the trough 100. In steps (d) and (e), the garment 50 is folded along a longitudinally extending first fold line 61 so as to position the first waist side region 60 over the waist center region 64. The first fold line 61 is adjacent the first side wall 104. In steps (f) and (g), the garment 50 is folded along a longitudinally extending second fold line 63 so as to position the second waist side region 62 over the waist center region 64. The second fold line 63 is adjacent the second side wall 106. After the garment 50 is thus folded twice in the transverse direction 53, the garment in particular embodiments exits the trough 100. In particular embodiments, the fully folded garment 80 exits the trough directly into a stacker (not shown). Note that step (b) can either occur before steps (d)-(g) or after steps (d)-(g).

In particular embodiments in which the trough width 105 extends in the machine direction 22, the trough 100 moves in the machine direction 22. In particular embodiments of such a configuration, the trough 100 orbits about an axis of rotation 120 during the folding of the garment 50 along the first and second fold lines 61, 63, the axis of rotation 120 extending in the cross-machine direction 24. One example of this configuration is a large folding drum 113, as employed in the configuration of FIGS. 11-13. In this example, a series of troughs 100 are spaced circumferentially around the folding drum 113.

Figure 11:
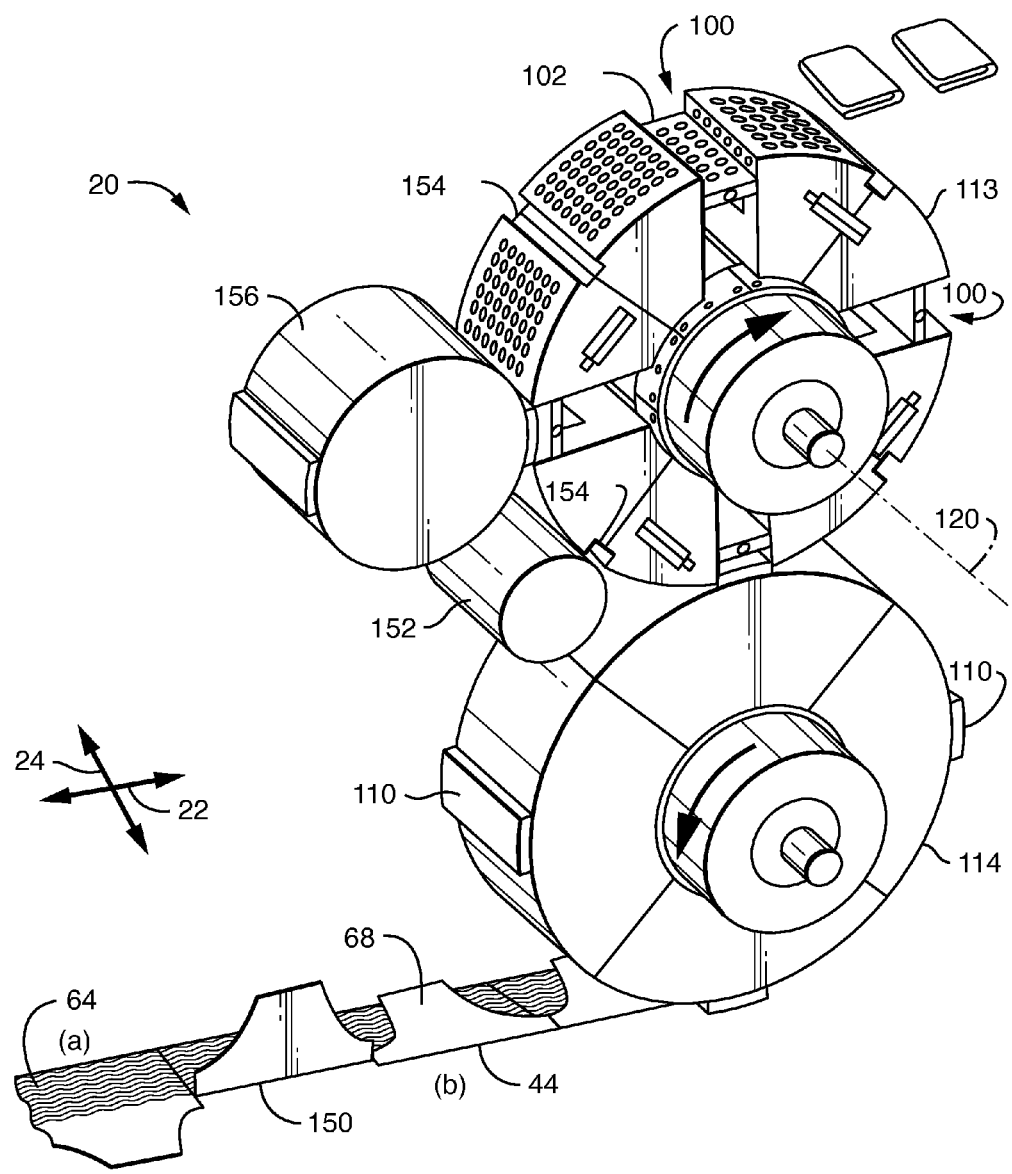
FIG. 11 representatively illustrates a perspective view of another embodiment of the method of the present invention.

In this embodiment, an interconnected series 150 is delivered to the folding drum 112, such as via a transfer drum 114. In the embodiment of FIG. 11, each garment 50 in the interconnected series 150 is folded along the respective transversely extending fold line 44 prior to arrival at the folding drum 112. In particular embodiments, placing the waist center region 64 and crotch region 68 in the trough 100 (step (c)) includes pressing the waist center region 64 and the crotch region 68 into the trough (such as against the floor 102 of the trough 100) using a pressing mechanism 110, shown as a raised portion on the transfer drum 114. In this way, the center region 64 is temporarily compressedly sandwiched between the trough floor 102 and the pressing mechanism 110. Other configurations could be used for the pressing mechanism 110, such as a compressed stream of air, or other suitable structure as discussed above.

In particular embodiments, as is representatively illustrated in FIG. 11, each individual garment 50 is separated from the interconnected series 150 while positioned on the folding drum 113, such as via a cutter 152. During the cutting step, the cutter 152 can penetrate a recess 154 formed in the folding drum 113, and/or the cutter 152 can engage a cutting anvil formed in the folding drum 113. In particular embodiments, a restraining drum 156 can hold the garment securely in the trough 100 during the cutting step.

Figure 12:
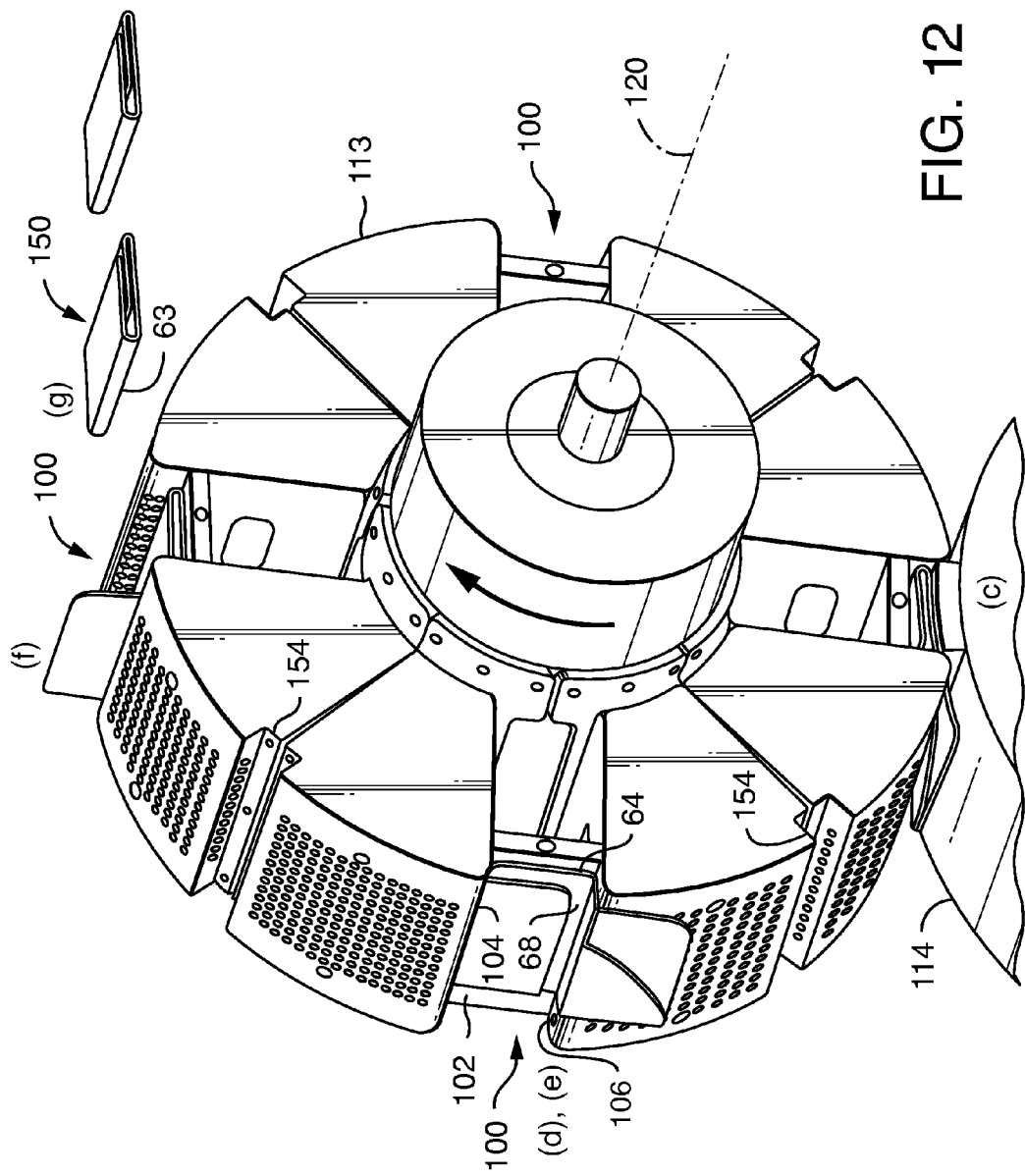
FIG. 12 representatively illustrates a perspective view of one embodiment of a portion of an apparatus suitable for use in conjunction with particular embodiments of the method of the present invention.
Figure 13:
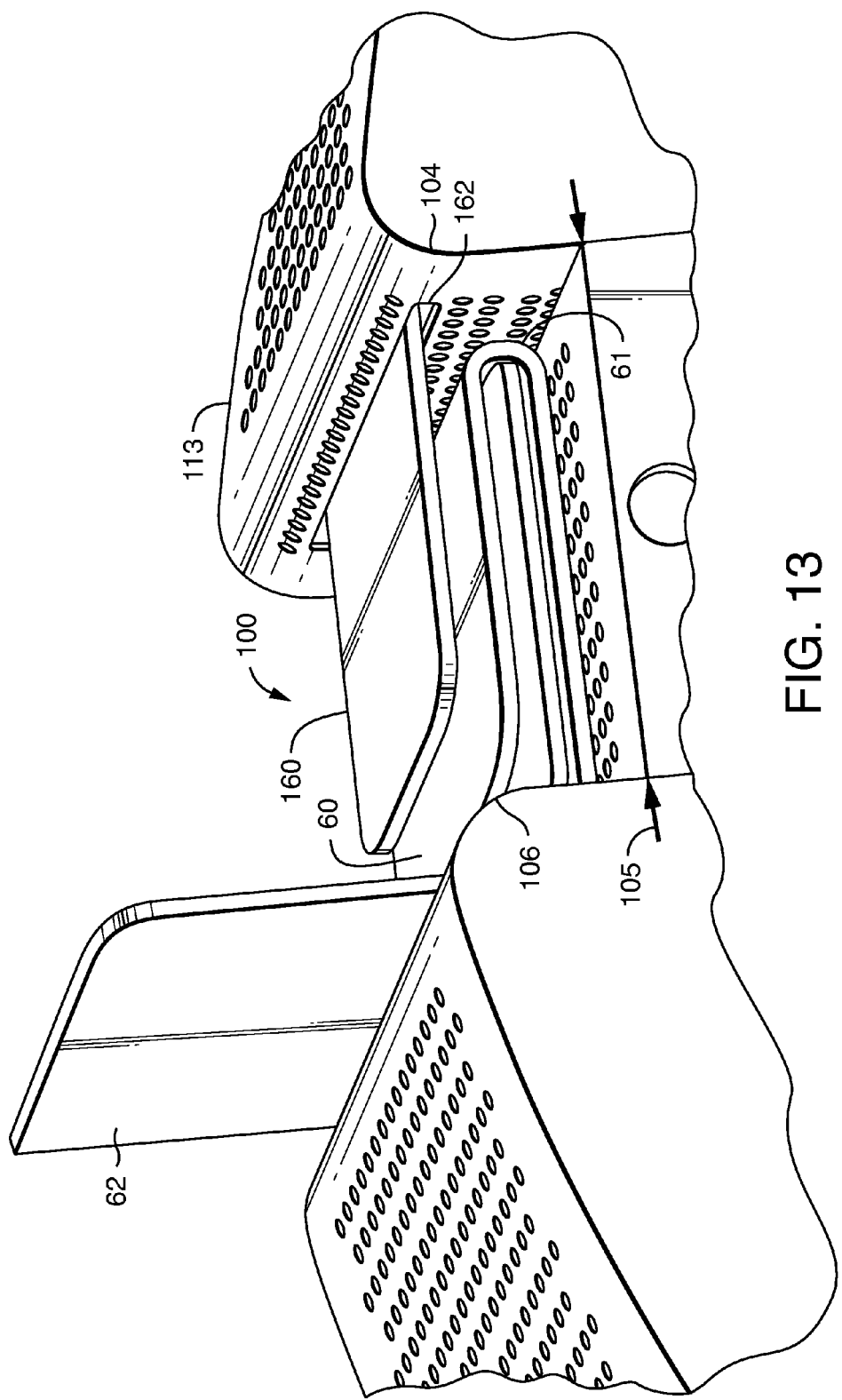
FIG. 13 representatively illustrates a close-up perspective view of the upper portion of the apparatus of FIG. 12, showing additional features and detail.
Figure 14:
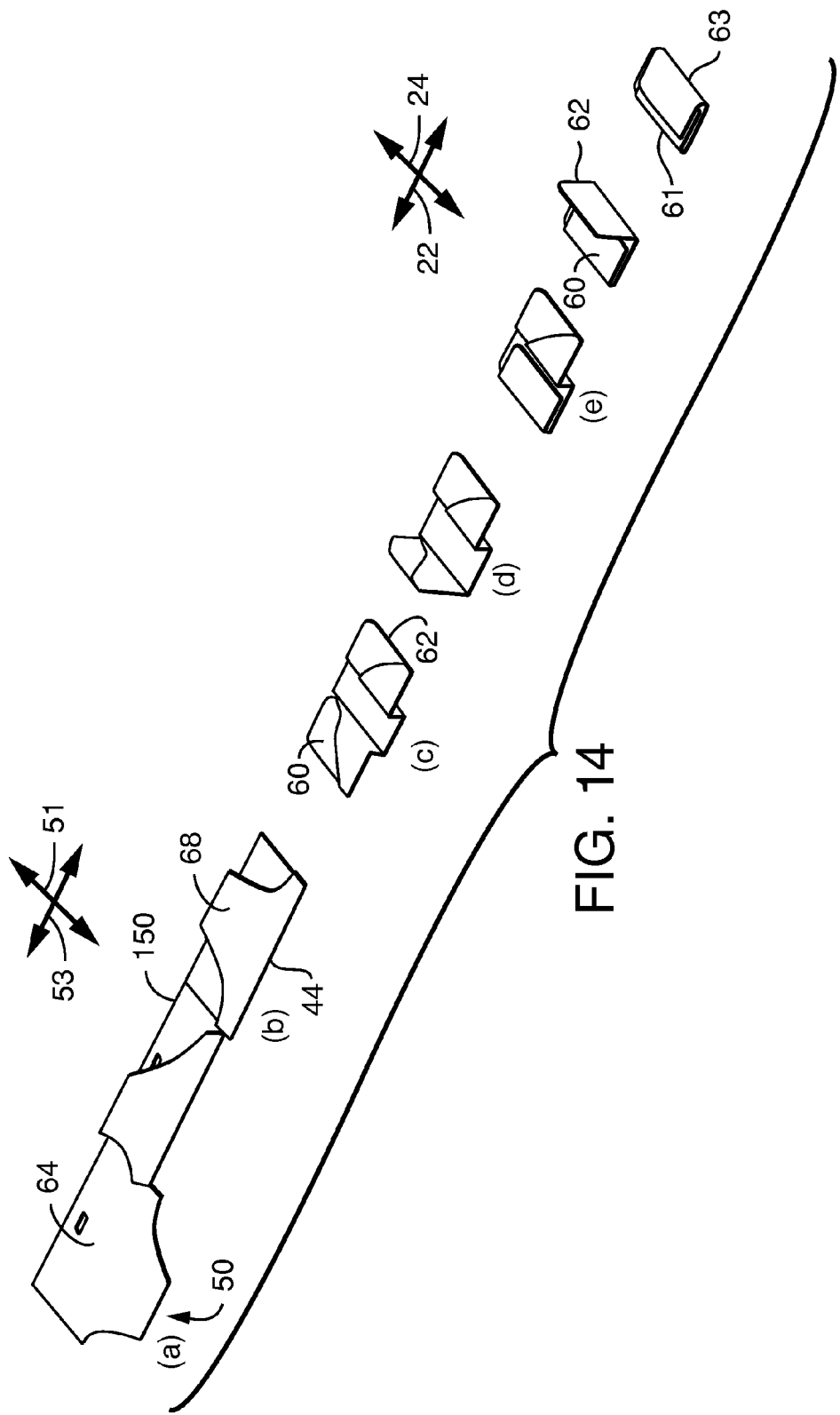
FIG. 14 representatively illustrates a perspective view of various stages of folding a garment in general accordance with the exemplary embodiments of FIGS. 11-13.

In the embodiment of FIGS. 11-13, the transverse folding of the first and second waist side regions 60, 62 can be accomplished by any of a variety of techniques. For example, folding the garment along the first and second fold lines 61, 63 can be accomplished via the use of protruding folding blades 160. For example, after the garments 50 have been separated from the interconnected series 150, a pair of folding blades can protrude into each trough through slots 162 present in respective side walls 104, 106. The motion of the blades is configured to make contact with the waist side regions 60, 62, and to fold the waist side regions 60, 62 over the waist center region 64. In an alternative example, folding the garment along the first and second fold lines is accomplished via a pair of compressed air blasts.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of folding a pant-like disposable absorbent garment, the method comprising:

providing said garment, said garment having a waist opening and two leg openings, said garment defining a longitudinal direction and a transverse direction, said garment defining a first waist side region adjacent a first side edge, a second waist side region adjacent a second side edge, a waist center region positioned transversely between the first waist side region and the second waist side region, and a crotch region longitudinally below said waist center region, the garment further including an absorbent core;

folding the garment along a transversely extending fold line so as to bring the crotch region into superposed relation with the waist center region;

providing a trough, the trough comprising a floor, a first side wall, and a second side wall, the trough defining a trough width extending from the first side wall to the second side wall;

pressing the waist center region into the trough; and folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the waist center region is in the trough.

2. The method of claim 1, wherein folding the garment along the transversely extending fold line occurs before folding the garment along the first and second fold lines.

3. The method of claim 1, wherein folding the garment along the transversely extending fold line occurs after folding the garment along the first and second fold lines.

4. The method of claim 1, wherein the absorbent core defines a longitudinally extending first core side edge and a longitudinally extending second core side edge, the core defining a maximum core width, wherein the maximum core width exceeds the trough width, such that the first fold line and the second fold line each extend into the absorbent core.

5. A method of folding a pant-like disposable absorbent garment, the method defining a machine direction and a cross-machine direction, the method comprising:
providing said garment, said garment having a waist opening and two leg openings, said garment defining a longitudinal direction and a transverse direction, said garment defining a first waist side region adjacent a first side edge, a second waist side region adjacent a second side edge, a waist center region positioned transversely between the first waist side region and the second waist side region, and a crotch region longitudinally below said waist center region, the garment further including an absorbent core;
folding the garment along a transversely extending fold line so as to bring the crotch region into superposed relation with the waist center region;
transporting said garment in the machine direction, such that the longitudinal direction of the garment is in parallel alignment with the machine direction during said transporting;
providing a trough that extends along the machine direction, the trough comprising a floor, a first side wall, and a second side wall, the trough defining a trough width extending along the floor from the first side wall to the second side wall, the trough width extending in a direction parallel to the cross-machine direction;
pressing the waist center region into the trough; and
folding the garment along a longitudinally extending first fold line so as to position the first waist side region over the waist center region, the first fold line being adjacent the first side wall, and folding the garment along a longitudinally extending second fold line so as to position the second waist side region over the waist center region, the second fold line being adjacent the second side wall, wherein both such folding steps occur while the waist center region is in the trough.

6. The method of claim 5, wherein folding the garment along the transversely extending fold line occurs before folding the garment along the first and second fold lines.

7. The method of claim 5, wherein folding the garment along the transversely extending fold line occurs after folding the garment along the first and second fold lines.

8. The method of claim 5, wherein the absorbent core defines a longitudinally extending first core side edge and a longitudinally extending second core side edge, the core defining a maximum core width, wherein the maximum core width exceeds the trough width, such that the first fold line and the second fold line each extend into the absorbent core.

9. The method of claim 5, wherein the floor of the trough moves in the machine direction.

10. The method of claim 9, wherein the floor of the trough extends in a flat plane.

11. The method of claim 9, wherein folding the garment along the first and second fold lines is accomplished via a pair of rotary tucking blade modules.

12. The method of claim 9, wherein the first side wall comprises a first side conveyor, and wherein the second side wall comprises a second side conveyer, and wherein the floor comprises a floor conveyor, wherein the first side conveyor, the second side conveyor, and the floor conveyor advance together in the machine direction.

13. The method of claim 9, wherein the both the first and second side walls are stationary, and wherein both the first and second side walls comprise vacuum holes through which vacuum forces are imparted, and wherein the vacuum forces attract the garment to the first and second side walls.

14. The method of claim 5, wherein placing the waist center region in the trough comprises pressing the waist center region against the floor of the trough using a pressing mechanism, such that the garment is compressedly sandwiched between the floor and the pressing mechanism.

15. The method of claim 5, the garment defining a crotch end and a waist end, wherein after folding the garment along the transversely extending fold line so as to bring the crotch region into superposed relation with the waist center region, the waist end and the crotch end are different distances from the transversely extending fold line.

* * * * *